(12) United States Patent
Jia et al.

(10) Patent No.: US 11,566,149 B2
(45) Date of Patent: *Jan. 31, 2023

(54) COATINGS CONTAINING POLYMER MODIFIED ENZYME FOR STABLE SELF-CLEANING OF ORGANIC STAINS

(71) Applicants: Toyota Motor Engineering & Manufacturing North America, Inc., Plano, TX (US); Toyota Motor Corporation, Toyota (JP); Regents of the University of Minnesota, Minneapolis, MN (US)

(72) Inventors: Hongfei Jia, Ann Arbor, MI (US); Ping Wang, North Oaks, MN (US); Liting Zhang, St. Paul, MN (US); Andreas Buthe, Steinfurt (DE); Xueyan Zhao, Circle Pines, MN (US); Songtao Wu, Ann Arbor, MI (US); Masahiko Ishii, Okazaki (JP); Minjuan Zhang, Ann Arbor, MI (US)

(73) Assignees: TOYOTA MOTOR CORPORATION; REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 639 days.

This patent is subject to a terminal disclaimer.

(21) Appl. No.: 16/258,567

(22) Filed: Jan. 26, 2019

(65) Prior Publication Data
US 2019/0144710 A1    May 16, 2019

Related U.S. Application Data

(63) Continuation of application No. 14/812,087, filed on Jul. 29, 2015, now Pat. No. 10,563,094, which is a continuation of application No. 13/229,277, filed on Sep. 9, 2011, now Pat. No. 9,121,016.

(51) Int. Cl.
| | | |
|---|---|---|
| C12N 9/14 | (2006.01) | |
| C12N 9/20 | (2006.01) | |
| C12N 9/54 | (2006.01) | |
| C12N 9/96 | (2006.01) | |
| C09D 5/16 | (2006.01) | |
| A61K 47/60 | (2017.01) | |
| C09D 7/40 | (2018.01) | |
| C12N 11/06 | (2006.01) | |
| C12N 11/089 | (2020.01) | |
| C09D 189/00 | (2006.01) | |
| C12N 9/26 | (2006.01) | |
| C08G 65/333 | (2006.01) | |
| C09D 5/02 | (2006.01) | |
| C09D 175/16 | (2006.01) | |

(52) U.S. Cl.
CPC ............ *C09D 189/00* (2013.01); *A61K 47/60* (2017.08); *C08G 65/33337* (2013.01); *C09D 5/024* (2013.01); *C09D 5/16* (2013.01); *C09D 7/40* (2018.01); *C09D 175/16* (2013.01); *C12N 9/14* (2013.01); *C12N 9/20* (2013.01); *C12N 9/2408* (2013.01); *C12N 9/2411* (2013.01); *C12N 9/54* (2013.01); *C12N 9/96* (2013.01); *C12N 11/06* (2013.01); *C12N 11/089* (2020.01); *C08L 2203/02* (2013.01); *C08L 2205/02* (2013.01)

(58) Field of Classification Search
None
See application file for complete search history.

(56) References Cited

U.S. PATENT DOCUMENTS

| | | |
|---|---|---|
| 3,220,928 A | 11/1965 | Brenner |
| 3,519,538 A | 7/1970 | Messing et al. |
| 3,672,955 A | 6/1972 | Stanley et al. |
| 3,705,938 A | 12/1972 | Hyman |
| 3,857,934 A | 12/1974 | Bernstein et al. |
| 3,935,862 A | 2/1976 | Kraskin |
| 3,957,974 A | 5/1976 | Hata |
| 4,016,043 A | 4/1977 | Schuurs et al. |
| 4,026,814 A | 5/1977 | Johnson et al. |
| 4,034,078 A | 7/1977 | Van Horn |
| 4,094,744 A | 6/1978 | Hartdegen et al. |
| 4,098,645 A | 7/1978 | Hartdegen et al. |
| 4,128,686 A | 12/1978 | Kyle et al. |
| 4,195,127 A | 3/1980 | Hartdegen et al. |

(Continued)

FOREIGN PATENT DOCUMENTS

| | | |
|---|---|---|
| AU | 2003304222 A1 | 1/2005 |
| AU | 2004257205 A1 | 1/2005 |
| AU | 2010201732 A1 | 5/2010 |
| CA | 2538124 A1 | 12/2004 |
| EP | 616033 A1 | 9/1994 |

(Continued)

OTHER PUBLICATIONS

G.W. Xing et al., "Influence of reaction conditions on syntheses of sweetener precursors catalyzed by thermolysin in tert-amyl alcohol", J. Peptide Res. vol. 52, Issue 4, pp. 300-304 (Date: 1998).

(Continued)

*Primary Examiner* — Robert J Yamasaki
*Assistant Examiner* — Charles Zoltan Constantine
(74) *Attorney, Agent, or Firm* — Dinsmore & Shohl LLP

(57) ABSTRACT

Bioactive coatings that are stabilized against inactivation by weathering are provided including a base associated with a chemically modified enzyme, and, optionally a first polyoxyethylene present in the base and independent of the enzyme. The coatings are optionally overlayered onto a substrate to form an active coating facilitating the removal of organic stains or organic material from food, insects, or the environment.

9 Claims, 5 Drawing Sheets

Specification includes a Sequence Listing.

(56) References Cited

U.S. PATENT DOCUMENTS

| | | |
|---|---|---|
| 4,195,128 A | 3/1980 | Hildebrand et al. |
| 4,195,129 A | 3/1980 | Fukui et al. |
| 4,229,536 A | 10/1980 | DeFilippi |
| 4,237,591 A | 12/1980 | Ginocchio |
| 4,297,137 A | 10/1981 | Sachetto et al. |
| 4,315,828 A | 2/1982 | Church |
| 4,322,308 A | 3/1982 | Hooper et al. |
| 4,385,632 A | 5/1983 | Odelhog |
| 4,539,982 A | 9/1985 | Bailly |
| 4,551,187 A | 11/1985 | Church et al. |
| 4,552,813 A | 11/1985 | Grams |
| 4,897,352 A | 1/1990 | Chonde et al. |
| 4,910,234 A | 3/1990 | Yamamori et al. |
| 5,112,602 A | 5/1992 | Miki et al. |
| 5,279,955 A | 1/1994 | Pegg et al. |
| 5,405,766 A | 4/1995 | Kallury et al. |
| 5,418,146 A | 5/1995 | Joo et al. |
| 5,420,179 A | 5/1995 | Fourquier et al. |
| 5,492,821 A | 2/1996 | Callstrom et al. |
| 5,496,710 A | 3/1996 | Nagao et al. |
| 5,508,185 A | 4/1996 | Kawamura et al. |
| 5,514,671 A | 5/1996 | Lyon et al. |
| 5,523,027 A | 6/1996 | Otsuka |
| 5,543,309 A | 8/1996 | Pischel |
| 5,559,163 A | 9/1996 | Dawson et al. |
| 5,593,398 A | 1/1997 | Weimer |
| 5,595,728 A | 1/1997 | Brockett et al. |
| 5,631,343 A | 5/1997 | Binns et al. |
| 5,643,559 A | 7/1997 | Eigen et al. |
| 5,719,039 A | 2/1998 | Dordick et al. |
| 5,728,544 A | 3/1998 | Tanaka et al. |
| 5,739,004 A | 4/1998 | Woodson |
| 5,739,023 A | 4/1998 | Harada et al. |
| 5,770,188 A | 6/1998 | Hamade et al. |
| 5,800,804 A | 9/1998 | Laney |
| 5,801,140 A | 9/1998 | Langley et al. |
| 5,817,300 A | 10/1998 | Cook et al. |
| 5,837,483 A | 11/1998 | Hirata |
| 5,868,720 A | 2/1999 | Van Antwerp |
| 5,876,802 A | 3/1999 | Brunnemann et al. |
| 5,912,408 A | 6/1999 | Trinh et al. |
| 5,914,367 A | 6/1999 | Dordick et al. |
| 5,919,689 A | 7/1999 | Selvig et al. |
| 5,942,435 A | 8/1999 | Wheeler |
| H1818 H | 11/1999 | Potgieter et al. |
| 5,981,743 A | 11/1999 | Gross et al. |
| 5,998,200 A | 12/1999 | Bonaventura et al. |
| 5,998,512 A | 12/1999 | Schloman |
| 6,030,933 A | 2/2000 | Herbots et al. |
| 6,060,043 A | 5/2000 | Hayden et al. |
| 6,080,391 A | 6/2000 | Tsuchiya et al. |
| 6,107,392 A | 8/2000 | Antonelli et al. |
| 6,150,146 A | 11/2000 | Hamade et al. |
| 6,265,191 B1 | 7/2001 | Mizusawa et al. |
| 6,291,582 B1 | 9/2001 | Dordick et al. |
| 6,303,290 B1 | 10/2001 | Liu et al. |
| 6,342,386 B1 | 1/2002 | Powers et al. |
| 6,472,493 B1 | 10/2002 | Huynh-Ba |
| 6,599,627 B2 | 7/2003 | Yeo et al. |
| 6,638,526 B1 | 10/2003 | Deussen et al. |
| 6,663,949 B1 | 12/2003 | Tanaka et al. |
| 6,713,660 B1 | 3/2004 | Roe et al. |
| 6,759,220 B1 | 7/2004 | LeJeune et al. |
| 6,818,212 B2 | 11/2004 | Johansen et al. |
| 6,844,028 B2 | 1/2005 | Mao et al. |
| 6,855,746 B2 | 2/2005 | Yoshitake et al. |
| 6,875,456 B2 | 4/2005 | Delest et al. |
| 6,881,711 B1 | 4/2005 | Gershun et al. |
| 6,905,733 B2 | 6/2005 | Russell et al. |
| 7,164,037 B2 | 1/2007 | Dietsche et al. |
| 7,335,400 B2 | 2/2008 | Russell et al. |
| 7,632,793 B2 | 12/2009 | Lang |
| 7,687,554 B2 | 3/2010 | Schellenberg et al. |
| 7,932,230 B2 | 4/2011 | McDaniel |
| 7,939,500 B2 | 5/2011 | McDaniel |
| 8,008,180 B2 | 8/2011 | Takahashi et al. |
| 8,011,381 B2 | 9/2011 | Newman et al. |
| 8,011,938 B2 | 9/2011 | Martin et al. |
| 8,222,015 B2 | 7/2012 | Wang et al. |
| 8,252,571 B2 | 8/2012 | Wang et al. |
| 8,311,297 B2 | 11/2012 | Du et al. |
| 8,324,295 B2 | 12/2012 | Jia et al. |
| 8,388,904 B1 | 3/2013 | McDaniel et al. |
| 8,394,618 B2 | 3/2013 | Buthe et al. |
| 8,497,248 B2 | 7/2013 | McDaniel |
| 8,618,066 B1 | 12/2013 | McDaniel |
| 8,679,825 B2 | 3/2014 | Wang et al. |
| 8,796,009 B2 | 8/2014 | Jia et al. |
| 8,932,717 B2 | 1/2015 | Lee et al. |
| 9,012,196 B2 | 4/2015 | Buthe et al. |
| 9,121,016 B2 | 9/2015 | Jia et al. |
| 9,193,873 B2 | 11/2015 | Wang et al. |
| 9,388,370 B2 | 7/2016 | Wu et al. |
| 9,428,740 B2 | 8/2016 | Buthe et al. |
| 9,828,597 B2 | 11/2017 | Wang et al. |
| 10,563,094 B2 | 2/2020 | Jia et al. |
| 2002/0019615 A1 | 2/2002 | Roe et al. |
| 2002/0192366 A1 | 12/2002 | Cramer et al. |
| 2003/0096383 A1 | 5/2003 | Shimizu et al. |
| 2003/0161789 A1 | 8/2003 | Ermantraut et al. |
| 2003/0166237 A1 | 9/2003 | Allermann et al. |
| 2004/0009159 A1 | 1/2004 | Polsenski et al. |
| 2004/0063831 A1 | 4/2004 | Sheppard et al. |
| 2004/0067279 A1 | 4/2004 | Delest et al. |
| 2004/0108608 A1 | 6/2004 | Ju et al. |
| 2004/0109853 A1 | 6/2004 | McDaniel |
| 2004/0175407 A1 | 9/2004 | McDaniel |
| 2004/0241497 A1 | 12/2004 | Sasaki et al. |
| 2004/0242831 A1 | 12/2004 | Tian et al. |
| 2004/0259746 A1 | 12/2004 | Warren et al. |
| 2005/0049166 A1 | 3/2005 | Huang |
| 2005/0058689 A1 | 3/2005 | McDaniel |
| 2005/0059128 A1 | 3/2005 | Arnold et al. |
| 2005/0079594 A1 | 4/2005 | Marion |
| 2005/0147579 A1 | 7/2005 | Schneider et al. |
| 2005/0176905 A1 | 8/2005 | Moon et al. |
| 2005/0255078 A1 | 11/2005 | Sakamoto et al. |
| 2005/0272141 A1 | 12/2005 | Crawford |
| 2006/0094626 A1 | 5/2006 | Horton |
| 2007/0093618 A1 | 4/2007 | Cheng et al. |
| 2007/0282070 A1 | 12/2007 | Adams et al. |
| 2008/0038241 A1 | 2/2008 | Schasfoort et al. |
| 2008/0108745 A1 | 5/2008 | Russell et al. |
| 2008/0119381 A1 | 5/2008 | Wang et al. |
| 2008/0145906 A1 | 6/2008 | Boucher et al. |
| 2008/0293117 A1 | 11/2008 | Wang et al. |
| 2008/0319193 A1 | 12/2008 | Grauert et al. |
| 2009/0023859 A1 | 1/2009 | Sakanoue et al. |
| 2009/0045056 A1 | 2/2009 | Berberich et al. |
| 2009/0104086 A1 | 4/2009 | Zax et al. |
| 2009/0238811 A1 | 9/2009 | McDaniel et al. |
| 2009/0274846 A1 | 11/2009 | Wada et al. |
| 2009/0325843 A1 | 12/2009 | Man et al. |
| 2010/0210745 A1 | 8/2010 | McDaniel et al. |
| 2010/0236582 A1 | 9/2010 | Heintz et al. |
| 2010/0248334 A1 | 9/2010 | McDaniel |
| 2010/0269731 A1 | 10/2010 | Tofte Jespersen et al. |
| 2010/0279376 A1 | 11/2010 | Wang et al. |
| 2010/0305014 A1 | 12/2010 | Miralles et al. |
| 2011/0076738 A1 | 3/2011 | Wang et al. |
| 2011/0195035 A1 | 8/2011 | Vondruska et al. |
| 2011/0240064 A1 | 10/2011 | Wales et al. |
| 2011/0250626 A1 | 10/2011 | Williams et al. |
| 2011/0311482 A1 | 12/2011 | Wang et al. |
| 2011/0312057 A1 | 12/2011 | Buthe et al. |
| 2012/0097194 A1 | 4/2012 | McDaniel et al. |
| 2012/0114961 A1 | 5/2012 | Lee et al. |
| 2012/0136119 A1 | 5/2012 | Davis et al. |
| 2012/0208923 A1 | 8/2012 | Jia et al. |
| 2012/0238005 A1 | 9/2012 | Wieland et al. |
| 2012/0276617 A1 | 11/2012 | Jia et al. |
| 2013/0065291 A1 | 3/2013 | Jia et al. |
| 2013/0137159 A1 | 5/2013 | Buthe et al. |
| 2014/0083324 A1 | 3/2014 | Wales et al. |

(56) References Cited

U.S. PATENT DOCUMENTS

| | | | |
|---|---|---|---|
| 2014/0141490 A1 | 5/2014 | Wang et al. |
| 2014/0193888 A1 | 7/2014 | Souter et al. |
| 2015/0175982 A1 | 6/2015 | Buthe et al. |
| 2015/0191607 A1 | 7/2015 | McDaniel |
| 2018/0044658 A1 | 2/2018 | Wang et al. |
| 2019/0153422 A1 | 5/2019 | Wang et al. |
| 2019/0153423 A1 | 5/2019 | Wang et al. |

FOREIGN PATENT DOCUMENTS

| | | | |
|---|---|---|---|
| EP | 0670380 A1 | 9/1995 |
| EP | 609691 B1 | 5/1998 |
| EP | 0896056 A1 | 2/1999 |
| EP | 1161502 B1 | 12/2004 |
| EP | 1551927 A1 | 7/2005 |
| EP | 1609826 A2 | 12/2005 |
| EP | 1644452 A2 | 4/2006 |
| EP | 1660596 A1 | 5/2006 |
| EP | 001661955 A1 | 5/2006 |
| EP | 2746378 A1 | 6/2014 |
| FR | 2832145 A1 | 5/2003 |
| GB | 1518746 A | 7/1978 |
| GB | 2410249 A | 7/2005 |
| GB | 2430436 A | 3/2007 |
| IL | 167413 A | 12/2010 |
| IL | 174122 A | 9/2011 |
| IL | 173658 A | 4/2012 |
| IL | 208769 A | 4/2012 |
| IL | 214668 A | 1/2013 |
| IL | 214669 A | 1/2013 |
| IL | 214670 A | 1/2013 |
| IL | 214671 A | 1/2013 |
| IL | 214672 A | 1/2013 |
| IL | 218129 A | 9/2013 |
| JP | S6377999 A | 4/1988 |
| JP | S63171678 A | 7/1988 |
| JP | S63202677 A | 8/1988 |
| JP | H01-285188 A | 11/1989 |
| JP | H0268117 A | 3/1990 |
| JP | H02-227471 A | 9/1990 |
| JP | 09-038183 A | 2/1997 |
| JP | 9-059470 | 3/1997 |
| JP | 2002526430 A | 8/2002 |
| JP | 2002-537470 A | 11/2002 |
| JP | 2002332739 A | 11/2002 |
| JP | 2004506089 A | 2/2004 |
| JP | 2009-511072 A | 3/2009 |
| JP | 2010-510380 A | 4/2010 |
| JP | 6096748 B2 | 3/2017 |
| JP | 6192022 B2 | 9/2017 |
| WO | 89/06278 A1 | 7/1989 |
| WO | 9516029 A1 | 6/1995 |
| WO | 9721804 A1 | 6/1997 |
| WO | 0050521 A1 | 8/2000 |
| WO | 0153010 A1 | 7/2001 |
| WO | 0216521 A1 | 2/2002 |
| WO | 2005/026269 A1 | 3/2005 |
| WO | 2005103372 A2 | 11/2005 |
| WO | 2007017701 A1 | 2/2007 |
| WO | 2008000646 A1 | 1/2008 |
| WO | 2008063902 A2 | 5/2008 |
| WO | 2009155115 A2 | 12/2009 |
| WO | 2012110563 A1 | 8/2012 |

OTHER PUBLICATIONS

U.S. Appl. No. 16/933,425, filed Jul. 20, 2020, Songtao Wu et al.
U.S. Appl. No. 12/820,101, filed Jun. 21, 2010, Hongfei Jia et al.
U.S. Appl. No. 13/229,277, filed Sep. 9, 2011, Hongfei Jia et al.
U.S. Appl. No. 13/567,341, filed Aug. 6, 2012, Songtao Wu et al.
U.S. Appl. No. 14/812,087, filed Jul. 29, 2015, Hongfei Jia et al.
U.S. Appl. No. 15/193,242, filed Jun. 27, 2016, Songtao Wu et al.
U.S. Appl. No. 15/468,694, filed Mar. 24, 2017, Hongfei Jia et al.
U.S. Appl. No. 15/810,700, filed Nov. 13, 2017, Andreas Buthe et al.
U.S. Appl. No. 15/810,713, filed Nov. 13, 2017, Andreas Buthe et al.
U.S. Appl. No. 16/258,560, filed Jan. 26, 2019, Andreas Buthe et al.
U.S. Appl. No. 16/258,561, filed Jan. 26, 2019, Songtao Wu et al.
U.S. Appl. No. 16/258,564, filed Jan. 26, 2019, Hongfei Jia et al.
U.S. Appl. No. 16/258,568, filed Jan. 26, 2019, Hongfei Jia et al.
U.S. Appl. No. 16/724,682, filed Dec. 23, 2019, Hongfei Jia et al.
U.S. Appl. No. 16/900,386, filed Jun. 12, 2020, Andreas Buthe et al.
U.S. Appl. No. 16/903,028, filed Jun. 16, 2020, Hongfei Jia et al.
Geraldine F. Drevon et al.; High-Activity Enzyme-Polyurethane Coatings; (2002) Biotechnology and Bioengineering, vol. 70, No. 7, Inc. pp. 785-794.
McDaniel, C.S. et al., "Biocatalytic paints and coatings," ACS Symposium Series (2009), 1002 (Smart Coatings II), pp. 239-249.
Johanna Mansfeld et al.; Site-specific and random immobilization of thermolysin-like proteases reflected in the thermal inactivation kinetics; Biotechnol. Appl. Biochem. (2000); pp. 189-195.
Minoru Kumakura et al.; 201. Interaction of Enzyme with Polymer Matrix in Immobilized Enzymes; Helvetica Chimica Acta; vol. 66; Fasc. 7; (1983); pp. 2044-2048.
Jaroslava Turková; Immobilization of Enzymes on Hydroxyalkyl Methacrylate Gels; Immobilization Techniques; Methods in Enzymology; (1976); 344: pp. 66-83.
Masahiro Takagi et al.; Nucleotide Sequence and Promoter Region for the Neutral Protease Gene from Bacillus stearothermophilus; Journal of Bacteriology, Sep. 1985, pp. 824-831.
Kuniyo Inouye et al.; Engineering, expression, purification, and production of recombinant thermolysin; Biotechnology Annual Review; vol. 13; ISSN 1387-2656; pp. 43-64 (2007).
Drevon, G. et al.; High-Activity Enzyme-Polyurethane Coatings, Biotechnology and Bioengineering, 79(7): 785-794, Sep. 30, 2002.
Mansfeld, et al.: The Stability of Engineered Thermostable Neutral Proteases from Bacillus Stearothermophilus in Organic Solvents and Detergents, Biotechnol. Bioeng. (2007) 97 (4): 672-679.
U.S. Appl. No. 12/643,666, filed Dec. 21, 2009.
U.S. Appl. No. 14/093,347, filed Nov. 29, 2013.
U.S. Appl. No. 14/097,128, filed Dec. 4, 2013.
Roberts, "Chemistry for peptide and protein PEGylation", Advanced Drug Delivery Reviews, vol. 54, 2002, p. 459-476.
Drevon, Géraldine F., "Enzyme Immobilization into Polymers and Coatings", University of Pittsburgh School of Engineering Dissertation, Nov. 2002.
Lt Col C. Carl Bostek, "Effective methods of in-line intravenous fluid warming at low to moderate infusion rates" Journal of the American Association of Nurse Anesthetists, vol. 60, No. 6, Dec. 1992.
Mansfeld, "The Stability of Engineered Thermostable Neutral Proteases from Bacillus Stearothermophilus in Organic Solvents and Detergents", Biotechnol. Bioeng. (2007) 97 (4): 672-679.
Sookkheo et al., Protein Expression and Purification (2000) 20: 142-151.
Novick, S. et al.; Protein-containing hydrophobic coatings and films, Biomaterials, 23: 441-448, 2002.
McDaniel, Steve et al., "Functional Additives: A Platform for Revitalizing the Paint and Coatings Industry", coatingsworld.com, Feb. 2010.
McDaniel, Steve, "Formulating with Bioengineered Additives: Enhancing the Performance and Functionality of Paints and Coatings", coatingsworld.com, Mar. 2010.
McDaniel, Steve, "Bioengineered Additives A Pipeline of Value Delivering Unique Functionality to Your Coating", Coatings World, vol. 15, No. 5, coatingsworld.com, May 2010.
Ciba Tinuvin 328 LIght Stabiliser, Ciba Specialty Chemicals Inc., Coating Effects Segment, Edition: 9.12.97 Basle.
Ciba Tinuvin 1130, Ciba Specialty Chemicals Inc., Coating Effects Segment, Edition: 15.12.97 Basle.
"Printing & Packaging Industrial Coatings Technical Data Sheet Tinuvin 400" BASF The Chemical Company, Dec. 2010 Rev 1.
R. Lambourne and T.A. Strivens (Editors), "Paint and surface coatings—Theory and practice" second edition, "5.18 Ultraviolet absorbers", 1999, pp. 195-196, William Andrew Publishing.

(56) References Cited

OTHER PUBLICATIONS

Dieter Stoye and Werner Freitag (Editors) "Paints, Coatings and Solvents", Second, Completely Revised Edition, "5. Paint Additives", 1998, p. 170, Wiley VCH.
Johan Bieleman (Editor), "Additives for Coatings", "8,2,3 Properties of Light Stabilizers", 2000, pp. 279-280, Wiley VCH.
H. Domininghaus, "Plastics for Engineers: Materials, Properties, Applications", 1993, p. 612, Carl Hanser.
Ruby Ynalvez et al., "Mini-review: toxicity of mercury as a consequence of enzyme alternation", Biometals (2016) 29: 781-788.
Manuela F. Frasco et al., "Mechanisms of cholinesterase inhibition by inorganic mercury", FEBS Journal 274 (2007) 1849-1861.
S. Gourinath et al. "Mercury induced modifications in the stereochemistry of the active site through Cys-73 in a serine protease—Crystal structure of the complex of a partially modified proteinase K with mercury at 1.8 Å resolution", Indian Journal of Biochemistry & Biophysics, vol. 38, Oct. 2001, pp. 298-302.
Annamaria Guagliardi et al., "Stability and activity of a thermostable malic enzyme in denaturants and water-miscible organic solvents" Eur. J. Biochem. 183, 25-30 (1989).
H.N. Fernley and P.G. Walker, "Studies on Alkaline Phosphatase: Inhibition by Phosphate Derivatives and the Substrate Specificity" Biochem. J. (1967) 104, 1011-1018.
Defoamer Technologies Agitanò, Münzing, PCA Apr. 2012.
Jose L. Muñoz-Muñoz et al., "Phenolic substrates and suicide inactivation of tyrosinase: kinetics and mechanism", Biochem. J. (2008) 416, 431-440.
Travis J. O'Brien et al., Effects of hexavalent chromium on the survival and cell cycle distribution of DNA repair-deficient S. cerevisiae, DNA Repair 1 (2002) 617-627, Elsevier.
Joan L. Huber et al., "Inactiviation of Highly Activated Spinach Leaf Sucrose-Phosphate Synthase by Dephosphorylation", Plant Physiol. (1991) 95, 291-297.
J.M. Widholm et al., "Inhibition of Cultured Cell Growth by Tungstate and Molybdate", Plant Cell Reports (1983) 2: 15-18, Springer-Verlag.
K.J. Lewis, J.H. Aklian, A. Sharaby, J.D. Zook, "Quantitative methods of predicting relative effectiveness of corrosion inhibitive coatings", Aircraft Engineering and Aerospace Technology, (1996) vol. 68 Issue: 3, pp. 12-22.
K.D. Ralston et al., "Electrochemical Evaluation of Constituent Intermetallics in Aluminum Alloy 2024-T3 Exposed to Aqueous Vanadate Inhibitors", Journal of The Electrochemical Society, 156 (4) C135-C146 (2009).
David B. Volkin, Henryk Mach and C. Russell Middaugh, "Review: Degradative Covalent Reactions Important to Protein Stability", Molecular Biotechnology 105, vol. 8, pp. 105-121 (1995).
"Emulsion Stability and Testing", Technical Brief 2011 vol. 2, Particle Sciences, Inc.
Solvent Miscibility Table / Solvent Polarity Chart (2013).
Muxin Liu, Michael A. Brook, Paul M. Zelisko and Amro N. Ragheb, "Chapter 11. Preparation and Applications of Silicone Emulsions Using Biopolymers", Colloidal Biomolecules, Biomaterials, and Biomedical Applications (2003).
Roman Pichot, "Stability and Characterisation of Emulsions in the presence of Colloidal Particles and Surfactants" A thesis submitted to the University of Birmingham for the degree of Doctor of Philosophy, Nov. 2010.
Mujumder et al. Int. J. Pharma Bio Sci. (2012) 3(1):610-627 (Year: 2012).
Mansfeld et al. Biotechnol. Bioengineer. (2007) 97: 672-679 (Year: 2007).
*Reactive Surfaces* v. *Toyota Motor Corporation*, Case IPR2016-01914, Paper No. 64 (PTAB, Mar. 1, 2017).
*Reactive Surfaces* v. *Toyota Motor Corporation*, Case IPR2016-01462, Paper No. 51 (PTAB, Jan. 12, 2018).
*Reactive Surfaces* v. *Toyota Motor Corporation*, Case IPR2017-00572, Paper No. 42 (PTAB, Feb. 5, 2018).

"Enzyme Nomenclature—Recommendations (1978) of the Nomenclature Committee of the international Union of Biochemistry", Academic Press, New York, (1979) pp. 234-239.
Diane K. Williiams et al., "Analysis of Latent Fingerprint Deposits by Infrared Microspectroscopy", Applied Spectroscopy, vol. 58, No. 3, (2004) pp. 313-316.
Gary Mong et al., "The Chemistry of Latent Prints from Children and Adults", The Chesapeake Examiner, Fall 1999, vol. 37, No. 2, pp. 4-6.
Deliang He et al., a-Amylase immobilized on bulk acoustic-wave sensor by UV-curing coating, Biochemical Engineering Journal 6 (2000) 7-11.
Ramotowski, R.S., in Advances in Fingerprint Technology, Chapter 3, Henry C Lee and R.E. Gaensslen, eds., CRC Press, Boca Raton, (2001) pp. 63-104.
Young Duk Kim et al., "Siloxane-Based Biocatalytic Films and Paints for Use as Reactive Coatings", Biotechnology and Bioengineering, vol. 72, No. 4, Feb. 20, 2001, pp. 475-482.
Enzyme Nomenclature 1984, "Recommendations of the Nomenclature Committee of the International Union of Biochemistry on the Nomenclature and Classificiation of Enzyme-Catalysed Reactions", Academic Press, New York (1984) pp. 270-279.
Keiji G. Asano et al., "Chemical Composition of Fingerprints for Gender Determination", J Forensic Sci, Jul. 2002, vol. 47, No. 4.
Kimone M. Antoine, "Chemical Differences are Observed in Children's Versus Adults' Latent Fingerprints as a Function of Time", J Forensic Sci, Mar. 2010, vol. 55, No. 2.
Science News Staff, "Fleeting Fingerprints May Yield Powerful New Tools", Apr. 15, 1997.
E. Roland Menzel, Fingerprint Detection with Lasers, Chapter 7 "Photoluminescence-Based Physical Treatments" Marcel Dekker, Inc. (1999) pp. 155-178.
Edward Bartick et al., "Spectrochemical Analysis and Hyperspectral Imaging of Latent Fingerprints", 16th Meeting of the International Association of Forensic Sciences, (2002) pp. 61-64.
Anil K. Jain et al., "Integrating Faces, Fingerprints, and Soft Biometric Traits for User Recognition", Proceedings of Biometric Authentication Workshop, LNCS 3087, pp. 259-269,Prague, May 2004.
B. Drozdowski et al.,. "Isopropyl Alcohol Extraction of Oil and Lipids in the Production of Fish Protein Concentrate from Herring", Journal of the American Oil Chemists' Society, (Jul. 1969) vol. 46, pp. 371-376.
Robert S. Ramotowski, Advances in Fingerprint Technology (2nd ed.), Chapter 3, "Composition of Latent Print Residue", In H.C. Lee and R.E. Gaensslen (Eds), Boca Raton: CRC Press, (2001) pp. 63-104.
Robert D. Olsen, Sr., "Scott's Fingerprint Mechanics" Chapter III, "Latent Fingerprints and Crime Scene Procedures", (1978) pp. 109-158.
G L Thomas and T E Reynoldson, "Some observations on fingerprint deposits", 1975 J. Phys. D: Appl. Phys. vol. 8 (1975) pp. 724-729.
Arthur and Elizabeth Rose, "The Condensed Chemical Dictionary (7th Ed.)", New York: Reinhold Publishing Co., pp. 80, 104, 222-223, 545, 556, 644-645, 691, 704, 716, 887, 891 (1961).
United States Department of Justice—Federal Bureau of Investigation, "The Science of Fingerprints—Classificiation and Uses", (Rev. Dec. 1984), Chapter XIII "Latent Impressions" pp. 170-174 (1985).
T. Kent (Ed.), Manual of Fingerprint Development Techniques—A Guide to the Selection and Use of Processes for the Development of Latent Fingerprints, 2nd Ed 1998 (Revised Jan. 2001), Sandridge: Home Office Police Scientific Develpment Branch, Chapter 1 "Latent Fingerprints", Sections 1.1, 1.2, 2.6 and "Visual Examination."
Kostadin Bobev, "Fingerprints and Factors Affecting Their Condition", J. Forensic Ident. 176/45 (2) 1995, pp. 176-183.
S.M. Bleay et al, "Fingerprint Source Book: manual of development techniques", London: Home Office—Centre for Applied Sciences and Technology. Chapter 2: Finger mark examination techniques within scope of ISO 17025, pp. 3-38 (2013) URL: http://www.gov.uk/government/publications/fingerprint-source-book.

(56) References Cited

OTHER PUBLICATIONS

B. Scruton et al, "The deposition of fingerprint films" 1975 J. Phys. D: Appl PHys. 8 pp. 714-723.
Robert D. Olsen, Sr., "Chemical Dating Techniques for Latent Fingerprints: A Preliminary Report", Identification News, (Feb. 1987) pp. 10-12.
B.M. Craig, "Refractive Indices of Some Saturated and Monoethenoid Fatty Acids and Methyl Esters", Canadian Journal of Chemistry, 1953, 31(5): pp. 499-504, https://doi.org/10.1139/v53-068.
A. Dorinson et al, "Refractive Indices and Densities of Normal Saturated Fatty Acids in the Liquid State", J. Am. Chem. Soc., 1942, 64(12), pp. 2739-2741.
Methods in Biotechnology, vol. 17, Microbial Enzymes and Biotransformations, Humana Press, Inc., Totowa, NJ, (2005), Scott J. Novick and J. David Rozzell, "Immobilization of Enzymes by Covalent Attachment."
David Rozzell and Fritz Wager (Eds), Biocatalytic Production of Amino Acids & Derivatives, Chapter 13 "Immobilized Enzymes: Techniques & Applications", Hanser Publishers (1992), pp. 306-319.
J. David Rozzell, "Immobilized Aminotransferases for Amino Acid Production", Methods in Enzymology, vol. 136, (1987) pp. 479-497.
Wang, P. et al, Enzyme Stabilization by Covalent Binding in Nanoporous Sol-Gel Glass for Nonaqueous Biocatalysis; Biotech. Bioeng. 2001, 74(3):249-255.
Kim Y. et al, Siloxane-based biocatalytic films and paints for use as reactive coatings, Biotechnology and Bioengineering 2001, 72(4), 475-482.
Bernfield, P. and Wan, J., "Antigens and Enzymes Made Insoluble by Entrapping Them into Lattices of Synthetic Polymers", Science 142 (3593), pp. 678-679 (1963).
Pollak et al., "Enzyme Immobilization by Condensation Copolymerization into Cross-Linked Polyacrylamide Gels", J. Am. Chem. Soc. 1980, 102, pp. 6324-6336.
Fukui et al., "Application of Photo-Crosslinkable Resin to Immobilization of an Enzyme", FEBS Letters, Jul. 1976, pp. 179-182, vol. 66, No. 2.
Fukui et al., "[20] Entrapment of Biocatalysts with Photo-Cross-Linkable Resin Prepolymers and Urethane Resin Prepolymers", Methods in Enzymology, vol. 135, 1987, pp. 230-252.
K. Yokozeki et al., "Application of Immobilized Lipase to Regio-Specific Interesterification of Triglyceride in Organic Solvent", European J Appl Microbiol Biotechnol (1982) 14:1-5.
Fusee, Murray C., "[42] Industrial Production of L-Aspartic Acid Using Polyurethane-Immobilized Cells Containing Aspartase", Methods in Enzymology, vol. 136, 1987, pp. 463-471.
G.J. Calton et al, "[45] Phenylalanine Production via Polyazetidine-Immobilized *Escherichia coli*: Optimization of Cell Loading" Methods in Enzymology, vol. 136, 1987, pp. 497-502.
Takagi, Toshio, "Confirmation of Molecular Weight of Aspergillus oryzae a-Amylase Using the Low Angle Laser Light Scattering Technique in Combination with High Pressure Silica Gel Chromatography", J. Biochem. vol. 89, No. 2, (1981), pp. 363-368.
E.A. Stein et al., "Alpha-Amylases as Calcium-Metalloenzymes. I. Preparation of Calcium-free Apoamylases by Chelation and Electrodialysis", Biochemistry, vol. 3, No. 1, Jan. 1964, pp. 56-61.
G. Muralikrishna et al., "Cereal a-amylases—an overview", Carbohydrate Polymers 60 (2005) pp. 163-173.
C.P. Poole, Jr. et al., "Introduction to Nanotechnology", John Wiley & Sons, 2003, Hoboken, NJ, Table 12.1 on p. 315.
L.R. Murphy et al., "Research Paper Protein hydraftion and unfolding", Folding & Design vol. 3, No. 2, 1998, pp. 105-118.
K. Won et al., "Effects of Water and Silica Gel on Enzyme Agglomeration in Organic Solvents", Biotechnol. Bioprocess Eng. 2001, vol. 6, No. 2, pp. 150-155.
R. Balasubramanian et al., "Extraction and Dispersion of Large Gold Nanoparticles in Nonpolar Solvents", J. Dispersion Science and Technology, vol. 22, No. 5, pp. 485-489 (2001).

M.S. Kunz et al., "Colloidal Gold Dispersions in Polymeric Matrices", Journal of Colloid and Interface Science 156, pp. 240-249 (1993).
A. Gole et al., "Pepsin-Gold Colloid Conjugates: Preparation, Characterization, and Enzymatic Activity", Langmuir 2001, 17, pp. 1674-1679.
A. Gole et al., "Studies on the formation of bioconjugates of Engoglucanase with colloidal gold", Colloids and Surfaces B: Biointerfaces 25 (2002) pp. 129-138.
Product Sheet by Novozymes A/S for Termamyl 120L, Type L pp. 1:4-4:4 (2002).
Chica et al., "Semi-rational Approaches to Engineering Enzyme Activity: Combining the Benfits of Directed Evolution and Rational Design", Curr Opin Biotechnol. Aug. 2005; 16(4);378-84. (Year: 2005), www.sciencedirect.com, 7 pages.
Singh et al., "Protein Engineering Approaches in the Post-Genomic Era", Current Protein Peptide Science, 2017, 18, 1-18 (Year: 2017), 11 pages.
Non-Final Office Action dated Jul. 21, 2020 for U.S. Appl. No. 16/258,560.
A. Koohestanian et al., "The Separation Method for Removing of Colloidal Particles from Raw Water", American-Eurasian J. Agric. & Environ. Sci., 4 (2): pp. 266-273 (2008).
W. Stöber et al., "Controlled Growth of Monodisperse Silica Spheres in the micron Size Range", Journal of Colloid and Interface Science 26, pp. 62-69 (1968).
M. Melchiors et al., "Recent developments in aqueous two-component polyurethane (2K-PUR) coatings", Progress in Organic Coatings 40 (2000), pp. 99-109, p. 100, first complete paragraph.
N.F. Almeida et al., "Immobilization of Glucose Oxidase in Thin Polypyrrole Films: Influence of Polymerization Conditions and Film Thickness on the Activity and Stability of the Immobilized Enzyme", Biotechnology and Bioengineering, vol. 42, pp. 1037-1045 (1993).
Green, Philip, "Fineness of Grind", European Coatings Journal, (2003), Issue 10, p. 53.
Third-Party Submission Under 37 CFR 1.290 dated Aug. 13, 2018 filed in U.S. Appl. No. 15/790,846, filed Oct. 23, 2017.
Third-Party Submission Under 37 CFR 1.290 dated Jul. 25, 2018 filed in U.S. Appl. No. 15/810,700, filed Nov. 13, 2017.
Third-Party Submission Under 37 CFR 1.290 dated Jul. 25, 2018 filed in U.S. Appl. No. 15/810,713, filed Nov. 13, 2017.
Non-Final Office Action dated Jan. 14, 2015 for U.S. Appl. No. 14/166,376.
Office Action Response filed Apr. 14, 2015 for U.S. Appl. No. 14/166,376.
Final Office Action dated Apr. 27, 2015 for U.S. Appl. No. 14/166,376.
Notice of Appeal and Pre-Brief Conference Request filed on Jun. 26, 2015 for U.S. Appl. No. 14/166,376.
Pre-Brief Appeal Conference Decision dated Jul. 21, 2015 for U.S. Appl. No. 14/166,376.
Notice of Allowance and Notice of Allowability dated Jul. 24, 2015 for U.S. Appl. No. 14/166,376.
*Reactive Surfaces* v. *Toyota Motor Corporation*, Case IPR2018-01194 filed Jun. 4, 2018, Petition for Inter Partes Review of U.S. Pat. No. 9,193,873 B2 with Declaration and Resume of Dr. David Rozzell, Ph.D.
"Enzyme Nomenclature—Recommendations (1978) of the Nomenclature Committee of the international Union of Biochemistry", Academic Press, New York, (1979) pp. 274-277.
*Reactive Surfaces* v. *Toyota Motor Corporation*, Case IPR2017-00572, Paper No. 42 (PTAB, Feb. 5, 2017).
Office Action Response filed Apr. 27, 2015 for U.S. Appl. No. 14/097,128.
Amendment and RCE Response filed Aug. 26, 2015 for U.S. Appl. No. 14/097,128.
Rebuttal document produced during oral deposition of Douglas Lamb, Ph.D.; May 10, 2017.
OMG Borchers GmbH; "Low molecular weight methyl polysiloxane for improved leveling and anti-float properties in solvent based coatings systems. 100% active"; Jul. 1, 2014.

(56) References Cited

OTHER PUBLICATIONS

OMG Borchers GmbH; "Low molecular weight methyl polysiloxane for improved leveling and anti-float properties in solvent based coatings systems. 100% active ingredient"; Aug. 28, 2009.
Reply Declaration of Eric Ray; Nov. 6, 2017.
*Reactive Surfaces* v. *Toyota Motor Corporation*, Case IPR2019-00867, Petition for Inter Partes Review of U.S. Pat. No. 9,428,740 B2, PTAB (Mar. 21, 2019).
Michelle V. Buchanan et al., "Chemical Characteristics of Fingerprints from Adults and Children," in Forencsic Evidence Analysis & Crime Scene Investigation, 2941 Proc. SPIE 89 (Feb. 5, 1997).
G.M. Mong et al. "Advanced Fingerprint Analysis Project Fingerprint Constituents," Technical Report, Pacific Northwest Laboratory (1999).
The American Heritage Stedman's Medical Dictionary, Second Edition, (Copyright 2007 and 2004, Houghton Mifflin), pp. 463-464, 884.
K. Hans Brockerhoff et al., "Lipolytic Enzymes", Academic Press, Inc., New York, New York, 1974, pp. 1-2, 4 and 8.
Shigeru Yamanaka et al., "[37] Regiospecific Interesterification of Triglyceride with Celite-Adsorbed Lipase," Methods in Enzymology, vol. 136, pp. 405-411 (1987).
Kiyotaka Oyama et al., "[46] Production of Aspartame by Immobilized Thermoase", Methods in Enzymology vol. 136, pp. 503-516 (1987).
Bo Chen et al., "Candida antarctica Lipase B Chemically Immobilized on Epoxy-Activated Micro- and Nanobeads: Catalysts for Polyester Synthesis", Biomacromolecules (published Jan. 16, 2008), vol. 9, Issue 2, pp. 463-471.
K. Bagi et al., "Immobilization and characterization of porcine pancreas lipase", Eyzyme and Microbial Technology vol. 20, pp. 531-535 (1997).
Recorded Assignment Documentation for U.S. Appl. No. 14/643,445, filed Mar. 10, 2015 (Exhibit 1003 from IPR2019-00867).
Declaration of Dr. David Rozzell, Ph.D. (Exhibit 1009 from IPR2019-00867)—May 14, 2018.
Non-Final Office Action dated Sep. 25, 2015 from U.S. Appl. No. 14/643,445, filed Mar. 10, 2015.
Office Action Response filed Dec. 29, 2015 from U.S. Appl. No. 14/643,445, filed Mar. 10, 2015.
Notice of Allowance and Notice of Allowability dated Apr. 28, 2016 from U.S. Appl. No. 14/643,445, filed Mar. 10, 2015.
As-filed U.S. Appl. No. 12/820,063, filed Jun. 21, 2010.
Deposition Transcript of Dr. Jonathan S. Dordick from IPR2016-01914 (Exhibit 1015 from IPR2019-00867)—Oct. 18, 2017.
Yang et al. Biotechnol Lett. Jul. 2010: 32(7): 951-6. Epub Mar. 8, 2010 (Year: 2010).
Chen et al. Biomacromolecules. Feb. 2008: 9(2): 463-71. Epub Jan. 16. (Year: 2008).
Yu et al. Biotechnol Lett. Apr. 2004; 26(8): 629-33 (Year: 2004).

SEQUENCE LISTING

```
<160> NUMBER OF SEQ ID NOS: 6

<210> SEQ ID NO 1
<211> LENGTH: 659
<212> TYPE: PRT
<213> ORGANISM: Bacillus subtilis

<400> SEQUENCE: 1

Met Phe Ala Lys Arg Phe Lys Thr Ser Leu Leu Pro Leu Phe Ala Gly
1               5                   10                  15

Phe Leu Leu Leu Phe His Leu Val Leu Ala Gly Pro Ala Ala Ala Ser
                20                  25                  30

Ala Glu Thr Ala Asn Lys Ser Asn Glu Leu Thr Ala Pro Ser Ile Lys
            35                  40                  45

Ser Gly Thr Ile Leu His Ala Trp Asn Trp Ser Phe Asn Thr Leu Lys
        50                  55                  60

His Asn Met Lys Asp Ile His Asp Ala Gly Tyr Thr Ala Ile Gln Thr
65                  70                  75                  80

Ser Pro Ile Asn Gln Val Lys Glu Gly Asn Gln Gly Asp Lys Ser Met
                85                  90                  95

Ser Asn Trp Tyr Trp Leu Tyr Gln Pro Thr Ser Tyr Gln Ile Gly Asn
                100                 105                 110
```

```
Arg Tyr Leu Gly Thr Glu Gln Glu Phe Lys Glu Met Cys Ala Ala
            115                 120                 125
Glu Glu Tyr Gly Ile Lys Val Ile Val Asp Ala Val Ile Asn His Thr
        130                 135                 140
Thr Ser Asp Tyr Ala Ala Ile Ser Asn Glu Val Lys Ser Ile Pro Asn
145                 150                 155                 160
Trp Thr His Gly Asn Thr Gln Ile Lys Asn Trp Ser Asp Arg Trp Asp
                165                 170                 175
Val Thr Gln Asn Ser Leu Leu Gly Leu Tyr Asp Trp Asn Thr Gln Asn
            180                 185                 190
Thr Gln Val Gln Ser Tyr Leu Lys Arg Phe Leu Asp Arg Ala Leu Asn
        195                 200                 205
Asp Gly Ala Asp Gly Phe Arg Phe Asp Ala Ala Lys His Ile Glu Leu
    210                 215                 220
Pro Asp Asp Gly Ser Tyr Gly Ser Gln Phe Trp Pro Asn Ile Thr Asn
225                 230                 235                 240
Thr Ser Ala Glu Phe Gln Tyr Gly Glu Ile Leu Gln Asp Ser Ala Ser
                245                 250                 255
Arg Asp Ala Ala Tyr Ala Asn Tyr Met Asp Val Thr Ala Ser Asn Tyr
            260                 265                 270
Gly His Ser Ile Arg Ser Ala Leu Lys Asn Arg Asn Leu Gly Val Ser
        275                 280                 285
Asn Ile Ser His Tyr Ala Ser Asp Val Ser Ala Asp Lys Leu Val Thr
    290                 295                 300
Trp Val Glu Ser His Asp Thr Tyr Ala Asn Asp Asp Glu Glu Ser Thr
305                 310                 315                 320
Trp Met Ser Asp Asp Asp Ile Arg Leu Gly Trp Ala Val Ile Ala Ser
                325                 330                 335
Arg Ser Gly Ser Thr Pro Leu Phe Phe Ser Arg Pro Glu Gly Gly Gly
            340                 345                 350
Asn Gly Val Arg Phe Pro Gly Lys Ser Gln Ile Gly Asp Arg Gly Ser
        355                 360                 365
Ala Leu Phe Glu Asp Gln Ala Ile Thr Ala Val Asn Arg Phe His Asn
    370                 375                 380
Val Met Ala Gly Gln Pro Glu Glu Leu Ser Asn Pro Asn Gly Asn Asn
385                 390                 395                 400
Gln Ile Phe Met Asn Gln Arg Gly Ser His Gly Val Val Leu Ala Asn
                405                 410                 415
Ala Gly Ser Ser Ser Val Ser Ile Asn Thr Ala Thr Lys Leu Pro Asp
            420                 425                 430
Gly Arg Tyr Asp Asn Lys Ala Gly Ala Gly Ser Phe Gln Val Asn Asp
        435                 440                 445
Gly Lys Leu Thr Gly Thr Ile Asn Ala Arg Ser Val Ala Val Leu Tyr
    450                 455                 460
Pro Asp Asp Ile Ala Lys Ala Pro His Val Phe Leu Glu Asn Tyr Lys
465                 470                 475                 480
Thr Gly Val Thr His Ser Phe Asn Asp Gln Leu Thr Ile Thr Leu Arg
                485                 490                 495
Ala Asp Ala Asn Thr Thr Lys Ala Val Tyr Gln Ile Asn Asn Gly Pro
            500                 505                 510
Glu Thr Ala Phe Lys Asp Gly Asp Gln Phe Thr Ile Gly Lys Gly Asp
        515                 520                 525
```

```
Pro Phe Gly Lys Thr Tyr Thr Ile Met Leu Lys Gly Thr Asn Ser Asp
    530                 535                 540

Gly Val Thr Arg Thr Glu Lys Tyr Ser Phe Val Lys Arg Asp Pro Ala
545                 550                 555                 560

Ser Ala Lys Thr Ile Gly Tyr Gln Asn Pro Asn His Trp Ser Gln Val
                565                 570                 575

Asn Ala Tyr Ile Tyr Lys His Asp Gly Ser Arg Val Ile Glu Leu Thr
                580                 585                 590

Gly Ser Trp Pro Gly Lys Pro Met Thr Lys Asn Ala Asp Gly Ile Tyr
            595                 600                 605

Thr Leu Thr Leu Pro Ala Asp Thr Asp Thr Thr Asn Ala Lys Val Ile
    610                 615                 620

Phe Asn Asn Gly Ser Ala Gln Val Pro Gly Gln Asn Gln Pro Gly Phe
625                 630                 635                 640

Asp Tyr Val Leu Asn Gly Leu Tyr Asn Asp Ser Gly Leu Ser Gly Ser
                645                 650                 655

Leu Pro His

<210> SEQ ID NO 2
<211> LENGTH: 1980
<212> TYPE: DNA
<213> ORGANISM: Bacillus subtilis

<400> SEQUENCE: 2
atgtttgcaa acgattcaa aacctcttta ctgccgttat tcgctggatt tttattgctg      60
tttcatttgg ttctggcagg accggcggct gcgagtgctg aaacggcgaa caaatcgaat     120
gagcttacag caccgtcgat caaaagcgga accattcttc atgcatggaa ttggtcgttc     180
aatacgttaa aacacaatat gaaggatatt catgatgcag atatacagc cattcagaca      240
tctccgatta ccaagtaaa ggaagggaat caaggagata aaagcatgtc gaactggtac      300
tggctgtatc agccgacatc gtatcaaatt ggcaaccgtt acttaggtac tgaacaagaa     360
tttaaagaaa tgtgtgcagc cgctgaagaa tatggcataa aggtcattgt tgacgcggtc     420
atcaatcata ccaccagtga ttatgccgcg atttccaatg aggttaagag tattccaaac     480
tggacacatg gaaacacaca aattaaaaac tggtctgatc gatgggatgt cacgcagaat     540
tcattgctcg gctgtatgat ctggaataca caaaatacac aagtacagtc ctatctgaaa     600
cggttcttag acagggcatt gaatgacggg gcagacggtt ttcgatttga tgccgccaaa     660
catatagagc ttccagatga tggcagttac ggcagtcaat tttggccgaa atcacaaat     720
acatctgcag agttccaata cggagaaatc ctgcaggata gtgcctccag agatgctgca     780
tatgcgaatt atatggatgt gacagcgtct aactatgggc attccataag gtccgcttta     840
aagaatcgta atctgggcgt gtcgaatatc tcccactatg catctgatgt gtctgcggac     900
aagctagtga catgggtaga gtcgcatgat acgtatgcca atgatgatga agagtcgaca     960
tggatgagcg atgatgatat ccgtttaggc tgggcggtga tagcttctcg ttcaggcagt    1020
acgcctcttt tcttttccag acctgaggga ggcggaaatg tgtgaggtt cccggggaaa     1080
agccaaatag gcgatcgcgg gagtgcttta tttgaagatc aggctatcac tgcggtcaat    1140
agatttcaca atgtgatggc tggacagcct gaggaactct cgaacccgaa tggaaacaac    1200
cagatatttt tgaatcagcg cggctcacat ggcgttgtgc tggcaaatgc aggttcatcc    1260
tctgtctcta tcaatacggc aacaaaattg cctgatggca ggtatgacaa taaagctgga    1320
gcgggttcat ttcaagtgaa cgatggtaaa ctgacaggca cgatcaatgc caggtctgta    1380
```

-continued

```
gctgtgctttt atcctgatga tattgcaaaa gcgcctcatg ttttccttga gaattacaaa    1440
acaggtgtaa cacattcttt caatgatcaa ctgacgatta ccttgcgtgc agatgcgaat    1500
acaacaaaag ccgtttatca aatcaataat ggaccagaga cggcgtttaa ggatggagat    1560
caattcacaa tcggaaaagg agatccattt ggcaaaacat acaccatcat gttaaaagga    1620
acgaacagtg atggtgtaac gaggaccgag aaatacagtt ttgttaaaag agatccagcg    1680
tcggccaaaa ccatcggcta tcaaaatccg aatcattgga gccaggtaaa tgcttatatc    1740
tataaacatg atgggagccg agtaattgaa ttgaccggat cttggcctgg aaaaccaatg    1800
actaaaaatg cagacggaat ttacacgctg acgctgcctg cggacacgga tacaaccaac    1860
gcaaaagtga ttttaataa tggcagcgcc caagtgcccg gtcagaatca gcctggcttt    1920
gattacgtgc taaatggttt atataatgac tcgggcttaa gcggttctct tccccattga    1980
```

<210> SEQ ID NO 3
<211> LENGTH: 548
<212> TYPE: PRT
<213> ORGANISM: Geobacillus stearothermophilus

<400> SEQUENCE: 3

```
Met Asn Lys Arg Ala Met Leu Gly Ala Ile Gly Leu Ala Phe Gly Leu
1               5                   10                  15

Leu Ala Ala Pro Ile Gly Ala Ser Ala Lys Gly Glu Ser Ile Val Trp
                20                  25                  30

Asn Glu Gln Trp Lys Thr Pro Ser Phe Val Ser Gly Ser Leu Leu Asn
            35                  40                  45

Gly Gly Glu Gln Ala Leu Glu Leu Val Tyr Gln Tyr Val Asp Arg
        50                  55                  60

Glu Asn Gly Thr Phe Arg Leu Gly Gly Arg Ala Arg Asp Arg Leu Ala
65                  70                  75                  80

Leu Ile Gly Lys Gln Thr Asp Glu Leu Gly His Thr Val Met Arg Phe
                85                  90                  95

Glu Gln Arg His His Gly Ile Pro Val Tyr Gly Thr Met Leu Ala Ala
                100                 105                 110

His Val Lys Asp Gly Glu Leu Ile Ala Leu Ser Gly Ser Leu Ile Pro
            115                 120                 125

Asn Leu Asp Gly Gln Pro Arg Leu Lys Lys Ala Lys Thr Val Thr Val
        130                 135                 140

Gln Gln Ala Glu Ala Ile Ala Glu Gln Asp Val Thr Glu Thr Val Thr
145                 150                 155                 160

Lys Glu Arg Pro Thr Thr Glu Asn Gly Glu Arg Thr Arg Leu Val Ile
                165                 170                 175

Tyr Pro Thr Asp Gly Thr Ala Arg Leu Ala Tyr Glu Val Asn Val Arg
            180                 185                 190

Phe Leu Thr Pro Val Pro Gly Asn Trp Val Tyr Ile Ile Asp Ala Thr
        195                 200                 205

Asp Gly Ala Ile Leu Asn Lys Phe Asn Gln Ile Asp Ser Arg Gln Pro
    210                 215                 220

Gly Gly Gly Gln Pro Val Ala Gly Ala Ser Thr Val Gly Val Gly Arg
225                 230                 235                 240

Gly Val Leu Gly Asp Gln Lys Tyr Ile Asn Thr Thr Tyr Ser Ser Tyr
                245                 250                 255

Tyr Gly Tyr Tyr Tyr Leu Gln Asp Asn Thr Arg Gly Ser Gly Ile Phe
            260                 265                 270
```

```
Thr Tyr Asp Gly Arg Asn Arg Thr Val Leu Pro Gly Ser Leu Trp Thr
            275                 280                 285

Asp Gly Asp Asn Gln Phe Thr Ala Ser Tyr Asp Ala Ala Val Asp
290                 295                 300

Ala His Tyr Tyr Ala Gly Val Val Tyr Asp Tyr Tyr Lys Asn Val His
305                 310                 315                 320

Gly Arg Leu Ser Tyr Asp Gly Ser Asn Ala Ala Ile Arg Ser Thr Val
                325                 330                 335

His Tyr Gly Arg Gly Tyr Asn Asn Ala Phe Trp Asn Gly Ser Gln Met
            340                 345                 350

Val Tyr Gly Asp Gly Asp Gly Gln Thr Phe Leu Pro Phe Ser Gly Gly
            355                 360                 365

Ile Asp Val Val Gly His Glu Leu Thr His Ala Val Thr Asp Tyr Thr
370                 375                 380

Ala Gly Leu Val Tyr Gln Asn Glu Ser Gly Ala Ile Asn Glu Ala Met
385                 390                 395                 400

Ser Asp Ile Phe Gly Thr Leu Val Glu Phe Tyr Ala Asn Arg Asn Pro
                405                 410                 415

Asp Trp Glu Ile Gly Glu Asp Ile Tyr Thr Pro Gly Val Ala Gly Asp
            420                 425                 430

Ala Leu Arg Ser Met Ser Asp Pro Ala Lys Tyr Gly Asp Pro Asp His
435                 440                 445

Tyr Ser Lys Arg Tyr Thr Gly Thr Gln Asp Asn Gly Gly Val His Thr
            450                 455                 460

Asn Ser Gly Ile Ile Asn Lys Ala Ala Tyr Leu Leu Ser Gln Gly Gly
465                 470                 475                 480

Val His Tyr Gly Val Ser Val Asn Gly Ile Gly Arg Asp Lys Met Gly
                485                 490                 495

Lys Ile Phe Tyr Arg Ala Leu Val Tyr Tyr Leu Thr Pro Thr Ser Asn
            500                 505                 510

Phe Ser Gln Leu Arg Ala Ala Cys Val Gln Ala Ala Asp Leu Tyr
            515                 520                 525

Gly Ser Thr Ser Gln Glu Val Asn Ser Val Lys Gln Ala Phe Asn Ala
530                 535                 540

Val Gly Val Tyr
545

<210> SEQ ID NO 4
<211> LENGTH: 1881
<212> TYPE: DNA
<213> ORGANISM: Geobacillus stearothermophilus

<400> SEQUENCE: 4
gatcaggaag cattgcgcta tggacgaagt gagcctcctt tcgttctcgg gatatagccg      60
aaaagaacca ggggaggaaa aacgaaagtc cgggccgtgc acggagggcg tgtcattgcc     120
gttcattttc ccaatacaat aaggatgact attttggtaa aattcagaat gtgaggaatc     180
atcaaataca tattcaagaa aggggaagag gagaatgaac aaacgggcga tgctcggggc     240
gatcgggctg gcgttcggcc tgctggcggc gccgatcggc gcttcggcga aggggaatc      300 gatcgtctgg aacgaacaat ggaagacgcc gtcattcgtg tccggttcgt tgctaaacgg     360
aggggaacaa gcgctggaag agctcgttta tcaatacgtc gatcgggaaa acggcacatt     420
ccgcctcggc ggacgcgccc gcgaccgttt ggcgctgatc ggcaaacaga ctgacgaact     480
tggccatacc gtgatgcggt ttgaacagcg gcatcacggt ataccggttt acggcaccat     540
```

```
gctggctgcc catgtgaaag atggcgagct gatcgcgctg tcggggtctt taattcccaa      600
tttagacggc cagccgcggt tgaaaaaggc gaaaacggtc accgtccaac aggcggaagc      660
tattgccgag caagacgtaa cggagacagt gacgaaggag cggccgacaa ccgaaaacgg      720
cgagcggacg cggctcgtca tttacccgac tgatggcacg gcccgcctcg cttatgaagt      780
gaacgtccgc ttttaacac cggttcccgg caactgggtg tatatcattg atgcaaccga       840
tggggccatt ttgaataagt tcaaccaaat cgacagccgc cagccggcg gcgggcagcc        900 ggtcgccggc gcgtcgacgg tcggcgtggg ccggggtgtg ttgggggatc agaaatatat      960
caatacgacg tattcctcgt attacggcta ctactatttg caagacaata cgcgcggcag      1020
cggcattttt acgtatgacg gacgaaaccg caccgttttg cccggcagct tgtggaccga      1080
tggcgacaac caatttaccg ccagctatga cgcggcggcc gtggacgccc attattacgc      1140
cggcgtcgtg tatgattact acaaaaatgt gcacggccgg ctgagctatg acggcagcaa      1200
cgccgccatc cgttcgaccg tccattatgg ccgcggctac aacaacgcgt tttggaacgg      1260
ttcgcaaatg gtgtacggcg atggcgacgg acagacgttt tgccgttttt ccggcggcat      1320
tgacgtcgtg gggcatgagt tgacccatgc ggtgacggat tatacggccg ggcttgttta      1380
ccaaaacgaa tctggcgcca tcaatgaagc gatgtccgat ttttcggca cgctcgtgga      1440 gttctacgcc aaccgcaacc cggactggga gattggcgaa gacatttaca cgcctggggt      1500
cgccggcgat gcgctccgct cgatgtccga cccggcgaaa tacggcgatc cggatcatta      1560
ttccaaacgg tacaccggca cgcaagacaa cggcggcgtc catacaaaca gcggcatcat      1620
caataaagcg gcgtacttgc tcagccaagg cggcgtccat tatggcgtga gcgtcaacgg      1680
catcggccgc gacaaaatgg ggaaaatttt ctaccgggcg cttgtctact atttgacgcc      1740
gacgtcgaac ttcagccagc tgcgtgccgc ctgcgtgcaa gcggccgctg atttgtacgg      1800
gtcgacaagc caagaagtca actcggtgaa acaggcgttc aatgcggttg gagtgtatta      1860
agacgatgag gtcgtacgcg t                                                1881
```

<210> SEQ ID NO 5
<211> LENGTH: 298
<212> TYPE: PRT
<213> ORGANISM: Aspergillis niger

<400> SEQUENCE: 5

```
Met Phe Leu Arg Arg Glu Phe Gly Ala Val Ala Ala Leu Ser Val Leu
1               5                   10                  15

Ala His Ala Ala Pro Ala Pro Ala Pro Met Gln Arg Arg Asp Ile Ser
                20                  25                  30

Ser Thr Val Leu Asp Asn Ile Asp Leu Phe Ala Gln Tyr Ser Ala Ala
            35                  40                  45

Ala Tyr Cys Ser Ser Asn Ile Glu Ser Thr Gly Thr Thr Leu Thr Cys
        50                  55                  60

Asp Val Gly Asn Cys Pro Leu Val Glu Ala Gly Ala Thr Thr Ile
65                  70                  75                  80

Asp Glu Phe Asp Asp Ser Ser Tyr Gly Pro Thr Gly Phe Ile
                85                  90                  95

Ala Val Asp Pro Thr Asn Glu Leu Ile Val Leu Ser Phe Arg Gly Ser
            100                 105                 110

Ser Asp Leu Ser Asn Trp Ile Ala Asp Leu Asp Phe Gly Leu Thr Ser
        115                 120                 125
```

Val Ser Ser Ile Cys Asp Gly Cys Glu Met His Lys Gly Phe Tyr Glu
    130                 135                 140

Ala Trp Glu Val Ile Ala Asp Thr Ile Thr Ser Lys Val Glu Ala Ala
145                 150                 155                 160

Val Ser Ser Tyr Pro Asp Tyr Thr Leu Val Phe Thr Gly His Ser Tyr
                165                 170                 175

Gly Ala Ala Leu Ala Ala Val Ala Ala Thr Val Leu Arg Asn Ala Gly
            180                 185                 190

Tyr Thr Leu Asp Leu Tyr Asn Phe Gly Gln Pro Arg Ile Gly Asn Leu
        195                 200                 205

Ala Leu Ala Asp Tyr Ile Thr Asp Gln Asn Met Gly Ser Asn Tyr Arg
    210                 215                 220

Val Thr His Thr Asp Asp Ile Val Pro Lys Leu Pro Pro Glu Leu Leu
225                 230                 235                 240

Gly Tyr His His Phe Ser Pro Glu Tyr Trp Ile Thr Ser Gly Asn Asp
                245                 250                 255

Val Thr Val Thr Thr Ser Asp Val Thr Glu Val Val Gly Val Asp Ser
            260                 265                 270

Thr Asp Gly Asn Asp Gly Thr Leu Leu Asp Ser Thr Thr Ala His Arg
        275                 280                 285

Trp Tyr Thr Ile Tyr Ile Ser Glu Cys Ser
    290                 295

<210> SEQ ID NO 6
<211> LENGTH: 897
<212> TYPE: DNA
<213> ORGANISM: Aspergillis niger

<400> SEQUENCE: 6
atgtttctcc gcagggaatt tggggctgtt gcagccctat ctgtgctggc ccatgctgct    60
cccgcacctg ctccgatgca gcgtagagac atctcctcta ccgtcttgga caatatcgac   120
ctcttcgccc aatacagtgc agcagcttac tgctcctcca acatcgagtc caccggcacg   180
actctgacct gcgacgtagg caattgccct ctcgtcgagg cagccggtgc cacgaccatc   240
gatgagtttg acgacagcag cagctacggc gacccgacgg ggttcatcgc cgttgacccg   300
acgaacgagt tgatcgttct gtctttccgg ggtagttccg acctctcgaa ctggattgcc   360
gacctagact tcggcctcac ctccgtaagc agcatctgtg atggctgtga gatgcacaag   420
ggcttctatg aggcctggga agtcattgcc gacaccatca catccaaggt ggaggccgct   480
gtctccagct atccggacta caccctcgtg ttcaccggac acagctacgg cgctgcattg   540
gcggctgtcg cggccaccgt actccgcaac gccggataca ctcttgacct gtacaacttc   600
ggccagcccc gtatcggcaa ccttgcttta gctgactaca tcaccgacca aaacatgggc   660
agcaactacc gcgtcacgca caccgacgac atcgtgccta agctgcctcc ggagctgctg   720
ggctaccacc acttcagtcc ggagtactgg atcaccagcg gtaatgatgt gacggtgact   780
acgtcggacg tgaccgaggt tgtggggggtg gattcgacgg atgggaatga cggcacgctg   840
cttgacagta cgactgccca tcggtggtac acgatctaca ttagtgaatg ctcgtag      897

COATINGS CONTAINING POLYMER MODIFIED ENZYME FOR STABLE SELF-CLEANING OF ORGANIC STAINS

CROSS-REFERENCE TO RELATED APPLICATIONS

This application is a continuation of U.S. patent application Ser. No. 14/812,087 filed Jul. 29, 2015, which is a continuation of U.S. patent application Ser. No. 13/229,277 filed Sep. 9, 2011 (now U.S. Pat. No. 9,121,016), the entire contents of each of which are incorporated herein by reference.

FIELD

The present specification relates generally to coating compositions including active substances and methods of their use to facilitate removal of organic stains. In specific aspects, the specification relates to methods of improving dispersibility of a bioactive enzyme in a polymeric matrix that leads to both improved enzyme stability in the matrix and reduction of weathering.

BACKGROUND

Many outdoor surfaces are subject to stain or insult from natural sources such as bird droppings, resins, and insect bodies. As a result, the resulting stain often leaves unpleasant marks on the surface deteriorating the appearance of the products.

Traditional self-cleaning coatings and surfaces are typically based on water rolling or sheeting to carry away inorganic materials. These show some level of effectiveness for removal of inorganic dirt, but are less effective for cleaning stains from biological sources, which consist of various types of organic polymers, fats, oils, and proteins each of which can deeply diffuse into the subsurface of coatings. Prior art approaches aim to reduce the deposition of stains on a surface and facilitate its removal by capitalizing on the "lotus-effect" where hydrophobic, oleophobic and super-amphiphobic properties are conferred to the surface by polymeric coatings containing appropriate nanocomposites. An exemplary coating contains fluorine and silicon nanocomposites with good roll off properties and very high water and oil contact angles. When used on rough surfaces like sandblasted glass, nanocoatings may act as a filler to provide stain resistance. A drawback of these "passive" technologies is that they are not optimal for use in high gloss surfaces because the lotus-effect is based on surface roughness.

Photocatalytic coatings are promising for promoting self-cleaning of organic stains. Upon the irradiation of sun light, a photocatalyst such as $TiO_2$ chemically breaks down organic dirt that is then washed away by the water sheet formed on the super hydrophilic surface. As an example, the photocatalyst $TiO_2$ was used to promote active fingerprint decomposition of fingerprint stains in U.S. Pat. Appl. Publ. 2009/104086. A major drawback to this technology is its limitation to use on inorganic surfaces due to the oxidative impairment of the polymer coating by $TiO_2$. Also, this technology is less than optimal for automotive coatings due to a compatibility issue: $TiO_2$ not only decomposes dirt, but also oxidizes polymer resins in paint.

Therefore, there is a need for new materials or coatings that can actively promote the removal of organic stains on surfaces or in coatings and minimize the requirement for maintenance cleaning.

SUMMARY

The following summary is provided to facilitate an understanding of some of the innovative features unique to the present specification and is not intended to be a full description. A full appreciation of the various aspects of the specification can be gained by taking the entire specification, claims, drawings, and abstract as a whole.

A water stabilized active coating material is provided wherein the coating is capable of degrading a component of an organic stain following immersion of said coating in water for 30 minutes or more, optionally where the coating retains 50% or more activity following immersion in water for 30 minutes.

A coating includes a base and a protein associated with the base. A protein is optionally chemically modified with one or more polymeric moieties. The coating optionally further includes a first polyoxyethylene associated with the base, where the first polyoxyethylene is independent of the enzyme; wherein the base, the enzyme, and the first polyoxyethylene form a water-stabilized active coating composition.

A chemically modified enzyme is optionally a hydrolase such as a bacterial neutral thermolysin-like-protease, an amylase, or a lipase. The enzyme is chemically modified by a polymeric moiety, optionally by at least one molecule of polyoxyethylene. The polyoxyethylene optionally has a molecular weight between 1,000 and 20,000 Daltons. In some aspects, the polyoxyethylene further includes a succinimidyl ester prior to reaction with said enzyme. A polymeric moiety is optionally directly or indirectly covalently bound to an amino group on the enzyme such as a terminal amino group or on a lysine. In some aspects a polymeric moiety is directly or indirectly covalently bound to a cysteine within the enzyme. In some aspects, a polymeric moiety optionally has a molecular weight of 10,000 Daltons to 20,000 Daltons. Optionally, a polymeric moiety has a molecular weight of 10,000 Daltons or greater, optionally 12,000 Daltons or greater.

An enzyme dispersed in base to form a water-stabilized active coating composition includes particles of protein that contain one or more protein molecules. The average particle diameter is optionally from 1 nanometer to 1 micrometer or any value or range therebetween.

A water-stabilized active coating material optionally is covalently attached to at least one component of the base or is non-covalently adhered to or admixed into the base. Such coatings when present on a substrate optionally have a surface activity of 0.0075 Units/$cm^2$ or greater when the coating includes a thermolysin as an enzyme. A base is optionally a one or two part solvent borne system, optionally including a polyurethane.

A process of stabilizing the activity of an enzyme against water weathering in a coating composition is provided including providing a water-stabilized active coating material is provide that includes associating one or more polymeric moieties with an enzyme to form a chemically modified enzyme and dispersing the chemically modified enzyme in a base to form a water-stabilized active coating material. The dispersing optionally results in protein particles with an average particle diameter from 1 nanometer to 1 micrometer, or any value or range therebetween. A process optionally includes coating a substrate with the active coating material such that the enzyme is capable of enzymatically degrading a component of an organic stain in contact with the active coating material.

DETAILED DESCRIPTION

Figure 1:
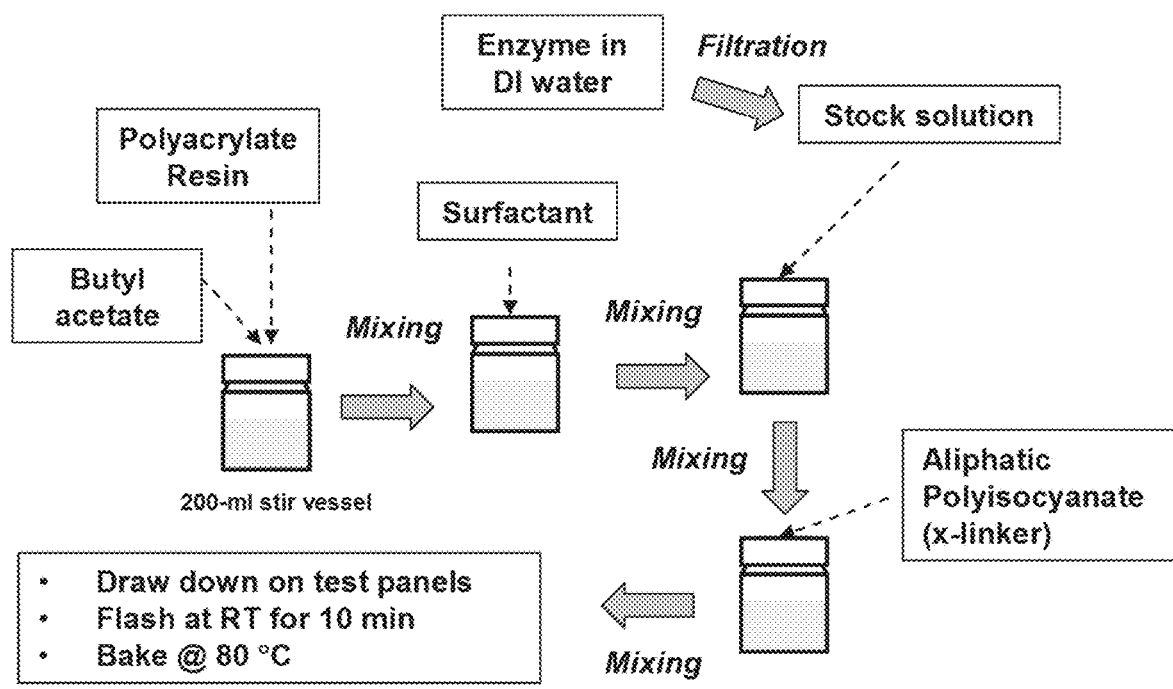
FIG. 1 is a schematic for forming a water-stabilized active coating composition according to one aspect.

The following description is merely exemplary in nature and is in no way intended to limit the scope of the claims, their application, or uses, which may, of course, vary. The specification is described with relation to the non-limiting definitions and terminology included herein. These definitions and terminology are not designed to function as a limitation on the scope or practice of the claims but are presented for illustrative and descriptive purposes only.

A composition useful as a coating is provided where one or more proteins associated with the coating material are optionally chemically modified so as to improve coating activity lifetime during and following exposure of a coating to water. The coatings provided herein are bioactive coatings that have several advantages over other coating materials in that they present improved lifetime after weathering and easy renewal of bioactivity by mild abrasion of the coating. Use of coatings containing chemically modified enzymes allows one to regularly renew the bioactive surface as well as improve other qualities such as shine, protection from the elements, and water runoff.

The coatings as provided herein demonstrate resistance to loss of activity due to weathering. Weathering as defined herein includes exposure to water, heat, UV light, or other insult either in the environment or in a laboratory. Coatings as provided herein have unexpected resistance to weathering by exposure to water, such as water immersion. As such, the term weathering includes immersion in water.

It is appreciated that the while the description herein is directed to coatings, the materials described herein may also be substrates or articles that do not require a coating thereon for promotion of organic stain removal. As such, the word "coating" as used herein means a material that is operable for layering on a surface of one or more substrates, or may comprise the substrate material itself. In some aspects, a "coating" is exclusive of a substrate such that it is a material that may be used to overlay a substrate. As such, the methods and compositions disclosed herein are generally referred to as an enzyme associated with a coating for exemplary purposes only. One of ordinary skill in the art appreciates that the description is equally applicable to substrates themselves.

The provided coatings are based on the catalytic activity of an enzyme to selectively degrade components of organic stains, thus, promoting active stain removal. Organic stains illustratively include organic polymers, fats, oils, or proteins. Inventive compositions and processes are provided for the active breakdown of organic stains by a water-stabilized active coating. Coating materials of the prior art have the capability to degrade organic stains, but the inventors unexpectedly discovered that these coatings are rapidly inactivated upon exposure to water such that the expected life of the coating is reduced to the point of uselessness in the field. Among the nearly infinite possible mechanisms of promoting stability of coating bioactivity, the inventors discovered that the addition of one or more polymeric moieties on or with an enzyme prior to incorporation with a base provides for dramatically improved water-stability of the resulting coating material.

A water-stabilized bioactive coating material composition is provided including a base with an associated chemically modified enzyme or with an enzyme intermixed with a polymeric moiety, and optionally a first polyoxyethylene also associated with the base, where the first polyoxyethylene is independent of the enzyme (i.e. not covalently linked to the enzyme). A composition has utility as a coating for the self-cleaning of organic stains such as food stains, insect stains, fingerprints, and other environmental or artificial insults.

A composition is a water-stabilized coating. The term "water-stabilized" denotes activity of the coating toward the self-cleaning or loosening of an associated organic stain, where the activity is increased by the presence of a chemically modified protein relative to the identical coating with a non-chemically modified protein. Water-stabilized optionally includes coatings that retain 50% to 90%, or any value or range therebetween, or more activity after coating immersion in water for 30 minutes. Water-stabilized optionally includes coatings that retain 15% or greater activity after coating immersion in water for 90 minutes.

In some aspects, a composition is a temporary coating. As used herein the term "temporary" is defined as operable for a time between 30 minutes and three months. It is appreciated that the outer limit of temporary is optionally defined by the environmental conditions a coating is subjected to. In some aspects, temporary is at or less than three months, optionally, less than 2 months, optionally less than 6, 5, 4, 3, 2, or 1 weeks, or any time or range of time therebetween. Optionally, temporary is at or less than 15, 14, 13, 12, 11, 10, 9, 8, 7, 6, 5, 4, 3, 2, or 1 day, or any time or range therebetween. In some aspects, the term "temporary" is any time between application of an inventive composition to a substrate and immersion or contact with water for 30, 60, or 90 minutes, or more. The reduced enzyme activity after the temporary time period is optionally renewed by abrasion of the surface of the coating to expose previously buried enzyme to the surface.

A composition includes a base material. As used herein a base material includes one or more organic polymeric materials. The combination of one or more of these materials and an enzyme form a water stabilized bioactive material (synonymously protein-polymer composite material) that can be used as a substrate material or a coating. Illustrative examples of base materials useful for association with one or more enzymes, optionally chemically modified enzymes, are illustrated in U.S. Patent Application Publication Nos. 2008/0293117 and 2010/0279376.

Preparation of water stabilized bioactive coating materials are illustratively achieved by association, optionally by dissolving, aqueous solutions of enzyme and one or more non-aqueous organic solvent-borne polymers. Enzyme is optionally dispersed in solvent-borne resin prior to curing. Dispersing of enzyme contrasts with forming large average aggregates (e.g. greater than 5 μm in diameter) of the enzyme that diminish the functionality of the enzymes and enzyme containing bioactive materials. Enzymes are optionally dispersed in the polymeric materials such that enzymes are unassociated with other bioactive proteins and/or form relatively small particles by average diameter (e.g. less than 5 μm) of associated proteins. Illustratively, the average particle size of enzyme particles in the protein-polymer composite material is less than 5 μm (average diameter) such as in the range of 1 nm to 5 μm. In some aspects, the average particle size is 5000, 4000, 3000, 2000, 1000, 900, 800, 700, 600, 500, 400, 300, 200, 100, 50, 25, 20, 15, 10, 5, 1 nm, or less or any value or range at or less than 0.1 nm to 5000 nm. In some aspects, the average particle size does not exceed 5, 4, 3, 2, or 1 μm. Optionally, the average particle size is 1 μm or less.

Curable protein-polymer compositions are optionally two-component solvent-borne (2K SB) compositions. Optionally, one component systems (1K) are similarly operable. Illustratively, an enzyme is entrapped in a coating material such as a latex or enamel paint, varnish, polyurethane gels, or other coating materials. Illustrative examples of incorporating enzymes into paints are presented in U.S. Pat. No. 5,998,200.

In two-component systems, the two components are optionally mixed shortly before use, for instance, application of the curable protein-polymer composition to a substrate to form an enzyme containing coating such as a bioactive clear coat. Generally described, the first component contains a crosslinkable polymer resin and the second component contains a crosslinker. Thus, the emulsion is a first component containing a crosslinkable resin and the crosslinker is a second component, mixed together to produce the curable protein-polymer composition.

A polymer resin included in methods and compositions as provided herein can be any film-forming polymer useful in coating or substrate compositions, illustratively clear coat compositions. Such polymers illustratively include, aminoplasts, melamine formaldehydes, carbamates, polyurethanes, polyacrylates, epoxies, polycarbonates, alkyds, vinyls, polyamides, polyolefins, phenolic resins, polyesters, polysiloxanes; and combinations of any of these or other polymers.

In some aspects, a polymer resin is crosslinkable. Illustratively, a crosslinkable polymer has a functional group characteristic of a crosslinkable polymer. Examples of such functional groups illustratively include acetoacetate, acid, amine, carboxyl, epoxy, hydroxyl, isocyanate, silane, vinyl, other operable functional groups, and combinations thereof.

Examples of organic crosslinkable polymer resins include aminoplasts, melamine formaldehydes, carbamates, polyurethanes, polyacrylates, epoxies, polycarbonates, alkyds, vinyls, polyamides, polyolefins, phenolic resins, polyesters, polysiloxanes, or combinations thereof.

A cross linking agent (crosslinker) is optionally included in the composition. The particular crosslinker selected depends on the particular polymer resin used. Non-limiting examples of crosslinkers include compounds having functional groups such as isocyanate functional groups, epoxy functional groups, aldehyde functional groups, or acid functionality.

In particular aspects of protein-polyurethane composite materials, a polymer resin is a hydroxyl-functional acrylic polymer and the crosslinker is a polyisocyanate.

A polyisocyanate, optionally a diisocyanate, is a crosslinker reacted with the hydroxyl-functional acrylic polymer according various aspects. Aliphatic polyisocyanates are optional polyisocyanates used in processes for making protein-polymer composite materials for clearcoat applications such as in automotive clearcoat applications. Non-limiting examples of aliphatic polyisocyanates illustratively include 1,4-butylene diisocyanate, 1,4-cyclohexane diisocyanate, 1,2-diisocyanatopropane, 1,3-diisocyanatopropane, ethylene diisocyanate, lysine diisocyanate, 1,4-methylene bis(cyclohexyl isocyanate), diphenylmethane 4,4'-diisocyanate, an isocyanurate of diphenylmethane 4,4'-diisocyanate, methylenebis-4,4'-isocyanatocyclohexane, 1,6-hexamethylene diisocyanate, an isocyanurate of 1,6-hexamethylene diisocyanate, isophorone diisocyanate, an isocyanurate of isophorone diisocyanate, p-phenylene diisocyanate, toluene diisocyanate, an isocyanurate of toluene diisocyanate, triphenylmethane 4,4',4''-triisocyanate, tetramethyl xylene diisocyanate, and meta-xylene diisocyanate.

Curing modalities are those typically used for conventional curable polymer compositions. Illustratively, curing is achieved by application of heat, UV light, or combinations thereof. Optionally, a coating composition is cured by exposure to oxygen or other atmosphere. Some aspects are cured spontaneously without necessary application of other curing affectors or conditions.

Protein-polymer composite materials are optionally thermoset protein-polymer composite materials. For example, a substrate or coating material is optionally cured by thermal curing. A thermal polymerization initiator is optionally included in a curable composition. Thermal polymerization initiators illustratively include free radical initiators such as organic peroxides and azo compounds. Examples of organic peroxide thermal initiators illustratively include benzoyl peroxide, dicumylperoxide, and lauryl peroxide. An exemplary azo compound thermal initiator is 2,2'-azobisisobutyronitrile.

Conventional curing temperatures and curing times can be used in processes according to various aspects. For example, the curing time at specific temperatures, or under particular curing conditions, is determined by the criteria that the cross-linker functional groups are reduced to less than 5% of the total present before curing. Cross-linker functional groups can be quantitatively characterized by FT-IR or other suitable method. For example, the curing time at specific temperatures, or under particular curing conditions, for a polyurethane protein-polymer composite can be determined by the criteria that the cross-linker functional group NCO is reduced to less than 5% of the total present before curing. The NCO group can be quantitatively characterized by FT-IR. Additional methods for assessing the extent of curing for particular resins are well-known in the art. Illustratively, curing may include evaporation of a solvent or by exposure to actinic radiation, such as ultraviolet, electron beam, microwave, visible, infrared, or gamma radiation.

One or more additives are optionally included for modifying the properties of the protein-polymer composite material and/or the admixture of organic solvent and polymer resin, the aqueous enzyme solution, the emulsion, and/or the curable composition. Illustrative examples of such additives include a UV absorbing agent, a plasticizer, a wetting agent, a preservative, a surfactant, a lubricant, a pigment, a filler, and an additive to increase sag resistance.

A substrate or coating including an enzyme is illustratively an admixture of a polymer resin, a surfactant and a non-aqueous organic solvent, mixed to produce an emulsion. The term "surfactant" refers to a surface active agent that reduces the surface tension of a liquid in which it is dissolved, or that reduces interfacial tension between two liquids or between a liquid and a solid.

Surfactants can be of any variety including amphoteric, silicone-based, fluorosurfactants, anionic, cationic and nonionic such as described in K. R. Lange, Surfactants: A Practical Handbook, Hanser Gardner Publications, 1999; and R. M. Hill, Silicone Surfactants, CRC Press, 1999, incorporated herein by reference. Examples of anionic surfactants illustratively include alkyl sulfonates, alkylaryl sulfonates, alkyl sulfates, alkyl and alkylaryl disulfonates, sulfonated fatty acids, sulfates of hydroxyalkanols, sulfosuccinic acid esters, sulfates and sulfonates of polyethoxylated alkanols and alkylphenols. Examples of cationic surfactants include quaternary surfactants and amineoxides. Examples of nonionic surfactants include alkoxylates, alkanolamides, fatty acid esters of sorbitol or manitol, and alkyl glucamides. Examples of silicone-based surfactants include siloxane polyoxyalkylene copolymers.

When a bioactive coating is contacted with biological material to produce a biological stain, the enzyme or combinations of enzymes contact the stain, or components thereof. The contacting allows the enzymatic activity of the enzyme to interact with and enzymatically alter the components of the stain improving its removal from the substrate or coating.

A composition includes at least one active protein that serves to produce the bioactive coating. An active protein is a macromolecule that has functional activity such as that of an enzyme illustratively a protease or hydrolase. A "protein" as defined herein as three or more natural, synthetic, or derivative amino acids covalently linked by a peptide bond and possessing the activity of an enzyme. Accordingly, the term "protein" as used herein includes between 3 and about 1000 or more amino acids or having a molecular weight in the range of about 150-350,000 Daltons. A protein is a molecule with a contiguous molecular sequence three amino acids or greater in length, optionally matching the length of a biologically produced proteinaceous molecule encoded by the genome of an organism. Examples of proteins include an enzyme, an antibody, a receptor, a transport protein, a structural protein, or a combination thereof. Proteins are capable of specifically interacting with another substance such as a ligand, drug, substrate, antigen, or hapten. It is appreciated that a protein is chemically modified by the addition of one or more homo or heteropolymeric moieties as described herein. The term "analogue" is exclusive of chemical modification with a homo or heteropolymeric group with the exception of biotinylation.

A protein is optionally modified from a naked polypeptide sequence such as by the addition or subtraction of one or more molecules of phosphorus, sulfur, or by the addition of a pendent group such as a biotin, avidin, fluorophore, lumiphore, or other pendent group suitable for purification, detection, or altering solubility or other characteristic of a protein.

The description herein is directed to a protein that is an enzyme, but it is appreciated that other protein active components are similarly operable herein. An enzyme is optionally a bioactive enzyme. A bioactive enzyme is capable of cleaving a chemical bond in a molecule that is found in a biological organism, the environment, or in food. A coating that is bioactive contains one or more bioactive enzymes. An enzyme is optionally a protease that is capable of cleaving a peptide bond illustratively including a bacterial protease, or analogue thereof. A protein that functions as an enzyme is optionally identical to the wild-type amino acid sequence encoded by a gene, a functional equivalent of such a sequence, or a combination thereof. A protein is referred to as "wild-type" if it has an amino acid sequence that matches the sequence of a protein as found in an organism in nature. It is appreciated that a protein is optionally a functional equivalent to a wild-type enzyme, which includes a sequence and/or a structural analogue of a wild-type protein's sequence and/or structure and functions as an enzyme. The functional equivalent enzyme may possess similar or the same enzymatic properties as a wild-type enzyme, such as catalyzing chemical reactions of the wild-type enzyme's EC classification, and/or may possess other enzymatic properties, such as catalyzing the chemical reactions of an enzyme related to the wild-type enzyme by sequence and/or structure. An enzyme encompasses its functional equivalents that catalyze the reaction catalyzed by the wild-type form of the enzyme (e.g., the reaction used for EC Classification). As an illustrative non-limiting example, the term "amylase" encompasses any functional equivalent of an amylase that retains amylase activity though the activity may be altered such as by increased reaction rates, decreased reaction rates, altered substrate preference, increased or decreased substrate binding affinity, etc. Examples of functional equivalents include mutations to a wild-type enzyme sequence, such as a sequence truncation, an amino acid substitution, an amino acid modification, and/or a fusion protein, etc., wherein the altered sequence functions as an enzyme.

An enzyme is immobilized into or on coatings and catalyzes the degradation of organic stain components into smaller molecules. Without being limited to one particular theory, the smaller product molecules are less strongly adherent to a surface or coating such that gravity or gentle rinsing such as with water, air, or other fluid promotes removal of the organic stain material from the coating. Thus, the provided aspects have utility as a composition and method for the active removal of organic stains from surfaces.

Enzymes are generally described according to standardized nomenclature as Enzyme Commission (EC) numbers. Examples of enzymes operable herein include: EC1, oxidoreductases; EC2, transferases; EC3, hydrolases; EC4, lyases; EC5, isomerases; or EC6, ligases. Enzymes in any of these categories can be included in a composition according to various aspects.

In some aspects, an included enzyme is a hydrolase such as a glucosidase, a protease, or a lipase. Non-limiting examples of glucosidases include amylases, chitinase, and lysozyme. Non-limiting examples of proteases include trypsin, chymotrypsin, thermolysin, subtilisin, papain, elastase, and plasminogen. Non-limiting examples of lipases include pancreatic lipase and lipoprotein lipase. Illustrative examples of proteins that function as enzymes are included in U.S. Patent Application Publication No: 2010/0210745.

Amylase is an enzyme present in some aspects of a coating composition. Amylases have activity that break down starch. Several types of amylases are operable herein illustratively including α-amylase (EC 3.2.1.1) responsible for endohydrolysis of (1→4)-alpha-D-glucosidic linkages in oligosaccharides and polysaccharides. α-Amylase is illustratively derived from *Bacillus subtilis* and has the sequence found at Genbank Accession No: ACM91731 (SEQ ID NO: 1), or an analogue thereof and encoded by the nucleotide sequence of SEQ ID NO: 2. A specific example is α-amylase from *Bacillus subtilis* available from Sigma-Aldrich Co., St. Louis, Mo. Additional α-amylases include those derived from *Geobacillus stearothermophilus* (Accession No: AAA22227), *Aspergillus oryzae* (Accession No: CAA31220), *Homo sapiens* (Accession No: BAA14130), *Bacillus amyloliquefaciens* (Accession No: ADE44086), *Bacillus licheniformis* (Accession No: CAA01355), or other organism, or analogues thereof. It is appreciated that β-amylases, γ-amylases, or analogues thereof from a variety of organisms are similarly operable in a protein-polymer composition.

Specific examples of amylase enzymes illustratively have 1000 U/g protease activity or more wherein one (1) U (unit) is defined as the amount of enzyme that will liberate the non-protein digestion product form potato starch of Zulkowsky (e.g. starch, treated with glycerol at 190° C.; *Ber. Deutsch. Chem. Ges,* 1880; 13:1395). Illustratively, the amylase has activity anywhere at or between 1,000 U/g to 500,000 U/g, or greater. It is appreciated that lower activities are operable.

A protease is optionally a bacterial metalloprotease such as a member of the M4 family of bacterial thermolysin-like proteases of which thermolysin is the prototype protease (EC 3.4.24.27) or analogues thereof. A protease is optionally the bacterial neutral thermolysin-like-protease (TLP) derived from *Bacillus stearothermophilus* (*Bacillus thermoproteolylicus* Var. Rokko) (illustratively sold under the trade name "THERMOASE C160" available from Amano Enzyme U.S.A., Co. (Elgin, Ill.)) or analogues thereof. A protease is optionally any protease presented in de Kreig, et al., *J Biol Chem,* 2000; 275(40):31115-20. Illustrative examples of a protease include the thermolysin-like-proteases from *Bacillis cereus* (Accession No. P05806), *Lactobacillis* sp. (Accession No. Q48857), *Bacillis megaterium* (Accession No. Q00891), *Bacillis* sp. (Accession No. Q59223), *Alicyclobacillis acidocaldarious* (Accession No. Q43880), *Bacillis caldolyticus* (Accession NO. P23384), *Bacillis thermoproteolyticus* (Accession No. P00800), *Bacillus stearothermophilus* (Accession No. P43133), *Bacillus subtilis* (Accession No. P06142), *Bacillus amyloliquefaciens* (Accession No. P06832), *Lysteria monocytogenes* (Accession No: P34025; P23224), among others known in the art.

A wild-type protease is a protease that has an amino acid sequence identical to that found in an organism in nature. An illustrative example of a wild-type protease is that found at GenBank Accession No. P06874 and SEQ ID NO: 3, with the nucleotide sequence encoding SEQ ID NO: 3 found in Takagi, M., et al., *J Bacteriol.,* 1985; 163(3):824-831 and SEQ ID NO: 4.

Methods of screening for protease activity are known and standard in the art. Illustratively, screening for protease activity in a protease protein or analogue thereof illustratively includes contacting a protease or analogue thereof with a natural or synthetic substrate of a protease and measuring the enzymatic cleavage of the substrate. Illustrative substrates for this purpose include casein of which is cleaved by a protease to liberate folin-positive amino acids and peptides (calculated as tyrosine) that are readily measured by techniques known in the art. The synthetic substrate furylacryloylated tripeptide 3-(2-furylacryloyl)-L-glycyl-L-leucine-L-alanine obtained from Bachem AG, Bubendorf, Switzerland is similarly operable.

Specific examples of proteases illustratively have 10,000 Units/g protease activity or more. In some aspects, a protease is a thermolysin wherein one (1) U (unit) is defined as the amount the enzyme that will liberate the non-proteinous digestion product from milk casein (final concentration 0.5%) to give Folin's color equivalent to 1 μmol of tyrosine per minute at the reaction initial reaction stage when a reaction is performed at 37° C. and pH 7.2. Illustratively, the protease activity is anywhere between 10,000 PU/g to 1,500,000 U/g inclusive or greater. It is appreciated that lower protease activities are operable. Protease activity is optionally in excess of 300,000 U/g. Optionally, protease activity is between 300,000 U/g and 2,000,000 U/g or higher.

A protein is optionally a lipase. A wild-type lipase is a lipase that has an amino acid sequence identical to that found in an organism in nature. An illustrative example of a wild-type lipase is that found at GenBank Accession No. ACL68189 and SEQ ID NO: 5. An exemplary nucleotide sequence encoding a wild-type lipase is found at Accession No. FJ536288 and SEQ ID NO: 6.

Lipase activity is illustratively defined in Units/gram. 1 Unit illustratively corresponds to the amount of enzyme that hydrolyzes 1 μmol acetic acid per minute at pH 7.4 and 40° C. using the substrate triacetin (Sigma-Aldrich, St. Louis, Mo., Product No. 90240). The lipase of SEQ ID NO: 5 may have an activity of 200 Units/gram.

Methods of screening for lipase activity are known and standard in the art. Illustratively, screening for lipase activity in a lipase protein or analogue thereof illustratively includes contacting a lipase or analogue thereof with a natural or synthetic substrate of a lipase and measuring the enzymatic cleavage of the substrate. Illustrative substrates for this purpose include tributyrin and triacetin both of which are cleaved by a triacylglycerol lipase to liberate butyric acid or acetic acid, respectively, that is readily measured by techniques known in the art.

A protein optionally functions with one or more cofactor ions or proteins. A cofactor ion is illustratively a zinc, cobalt, or calcium.

Cloning, expressing, and purifying any protein operable herein is achievable by methods ordinarily practiced in the art illustratively by methods disclosed in: Molecular Cloning: A Laboratory Manual, 2nd ed., vol. 1-3, ed. Sambrook et al., Cold Spring Harbor Laboratory Press, Cold Spring Harbor, N.Y., 1989; Current Protocols in Molecular Biology, ed. Ausubel et al., Greene Publishing and Wiley-Interscience, New York, 1992 (with periodic updates); and Short Protocols in Molecular Biology, ed. Ausubel et al., 52 ed., Wiley-Interscience, New York, 2002.

Naturally derived amino acids present in a protein illustratively include the common amino acids alanine, cysteine, aspartic acid, glutamic acid, phenylalanine, glycine, histidine, isoleucine, lysine, leucine, methionine, asparagine, proline, glutamine, arginine, serine, threonine, valine, tryptophan, and tyrosine. It is appreciated that less common derivatives of amino acids that are either found in nature or chemically altered are optionally present in a protein as well such as alpha-asparagine, 2-aminobutanoic acid or 2-aminobutyric acid, 4-aminobutyric acid, 2-aminocapric acid (2-aminodecanoic acid), 6-aminocaproic acid, alpha-glutamine, 2-aminoheptanoic acid, 6-aminohexanoic acid, alpha-aminoisobutyric acid (2-aminoalanine), 3-aminoisobutyric acid, beta-alanine, allo-hydroxylysine, allo-isoleucine, 4-amino-7-methylheptanoic acid, 4-amino-5-phenylpentanoic acid, 2-aminopimelic acid, gamma-amino-beta-hydroxybenzenepentanoic acid, 2-aminosuberic acid, 2-carboxyazetidine, beta-alanine, beta-aspartic acid, biphenylalanine, 3,6-diaminohexanoic acid, butanoic acid, cyclobutyl alanine, cyclohexylalanine, cyclohexylglycine, N5-aminocarbonylornithine, cyclopentyl alanine, cyclopropyl alanine, 3-sulfoalanine, 2,4-diaminobutanoic acid, diaminopropionic acid, 2,4-diaminobutyric acid, diphenyl alanine, N,N-dimethylglycine, diaminopimelic acid, 2,3-diaminopropanoic acid, S-ethylthiocysteine, N-ethylasparagine, N-ethylglycine, 4-aza-phenylalanine, 4-fluoro-phenylalanine, gamma-glutamic acid, gamma-carboxyglutamic acid, hydroxyacetic acid, pyroglutamic acid, homoarginine, homocysteic acid, homocysteine, homohistidine, 2-hydroxyisovaleric acid, homophenylalanine, homoleucine, homoproline, homoserine, homoserine, 2-hydroxypentanoic acid, 5-hydroxylysine, 4-hydroxyproline, 2-carboxyoctahydroindole, 3-carboxyisoquinoline, isovaline, 2-hydroxypropanoic acid (lactic acid), mercaptoacetic acid, mercaptobutanoic acid, sarcosine, 4-methyl-3-hydroxyproline, mercaptopropanoic acid, norleucine, nipecotic acid, nortyrosine, norvaline, omega-amino acid, ornithine, penicillamine (3-mercaptovaline), 2-phenylglycine, 2-carboxypiperidine, sarcosine (N-methylglycine), 2-amino-3-(4-sulfophenyl)propionic acid, 1-amino-1-carboxycyclopentane, 3-thienylalanine, epsilon-N-trimethyllysine, 3-thiazolylalanine, thiazolidine 4-carboxylic acid, alpha-amino-2,4-dioxopyrimidinepropanoic acid, and 2-naphthylalanine.

A protein is obtained by any of various methods known in the art illustratively including isolation from a cell or organism, chemical synthesis, expression of a nucleic acid sequence, and partial hydrolysis of proteins. Chemical methods of protein synthesis are known in the art and include solid phase peptide synthesis and solution phase peptide synthesis or by the method of Hackeng, T M, et al., *Proc Natl Acad Sci USA,* 1997; 94(15):7845-50. A protein may be a naturally occurring or non-naturally occurring protein. The term "naturally occurring" refers to a protein endogenous to a cell, tissue or organism and includes allelic variations. A non-naturally occurring protein is synthetic or produced apart from its naturally associated organism or is modified and is not found in an unmodified cell, tissue or organism.

Modifications and changes can be made in the structure of a protein and still obtain a molecule having similar characteristics as an active enzyme (e.g., a conservative amino acid substitution). For example, certain amino acids can be substituted for other amino acids in a sequence without appreciable loss of activity or optionally to reduce or increase the activity of an unmodified protein. Because it is the interactive capacity and nature of a protein that defines that protein's functional activity, certain amino acid sequence substitutions can be made in a protein sequence and nevertheless obtain a protein with like or other desired properties. Proteins with an amino acid sequence that is not 100% identical to that found in nature are termed analogues. An analogue optionally includes one or more amino acid substitutions, modifications, deletions, additions, or other change recognized in the art with the proviso that any such change produces a protein with the same type of activity (e.g. hydrolase) as the wild-type sequence. In making such changes, the hydropathic index, or the hydrophilicity of amino acids can be considered. In such changes, the substitution using amino acids whose hydropathic indices or hydrophilicity values are within ±2, those within ±1, and those within ±0.5 are optionally used.

Amino acid substitutions are optionally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gin, His), (Asp: Glu, Cys, Ser), (Gln: Asn), (Glu: Asp), (Gly: Ala), (His: Asn, Gin), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). In particular, aspects of the proteins can include analogues having about 50%, 60%, 70%, 80%, 90%, 95%, or 99% sequence identity to a wild-type protein.

It is further appreciated that the above characteristics are optionally taken into account when producing a protein with reduced or increased enzymatic activity. Illustratively, substitutions in a substrate binding site, exosite, cofactor binding site, catalytic site, or other site in a protein may alter the activity of the enzyme toward a substrate. In considering such substitutions the sequences of other known naturally occurring or non-naturally occurring like enzymes may be taken into account. Illustratively, a corresponding mutation to that of Asp213 in thermolysin is operable such as that done by Miki, Y, et al., *Journal of Molecular Catalysis B: Enzymatic,* 1996; 1:191-199. Optionally, a substitution in thermolysin of L144 such as to serine alone or along with substitutions of G8C/N60C/S65P are operable to increase the catalytic efficiency by 5-10 fold over the wild-type enzyme. Yasukawa, K, and Inouye, K, *Biochimica et Biophysica Acta (BBA)—Proteins & Proteomics,* 2007; 1774: 1281-1288. The mutations in the bacterial neutral protease from *Bacillus stearothermophilus* of N116D, Q119R, D150E, and Q225R as well as other mutations similarly increase catalytic activity. De Kreig, A, et al., *J. Biol. Chem.,* 2002; 277:15432-15438. De Kreig also teach several substitutions including multiple substitutions that either increase or decrease the catalytic activity of the protein. Id. and De Kreig, *Eur J Biochem,* 2001; 268(18):4985-4991. Other substitutions at these or other sites optionally similarly affect enzymatic activity. It is within the level of skill in the art and routine practice to undertake site directed mutagenesis and screen for subsequent protein activity such as by the methods of De Kreig, *Eur J Biochem,* 2001; 268(18):4985-4991.

A protein is optionally an analogue of a wild-type protein. An analogue of a protein has an amino acid sequence that when placed in similar conditions to a wild-type protein possess some level of the activity of a wild-type enzyme toward the same substrate. An analogue optionally has 500%, 250%, 200%, 150%, 110%, 99%, 98%, 97%, 96%, 95%, 94%, 93%, 92%, 91%, 90%, 85%, 80%, 75%, 70%, 60%, 50%, 25%, 10%, 5%, or any value or range of values therebetween, the activity of a wild-type protein. Any modification to a wild-type protein may be used to generate an analogue. Illustratively, amino acid substitutions, additions, deletions, cross-linking, removal or addition of disulfide bonds, or other modification to the sequence or any member of the sequence may be used to generate an analogue. An analogue is optionally a fusion protein that includes the sequences of two or more wild-type proteins, fragments thereof, or sequence analogues thereof.

Methods of screening for protein activity are known and standard in the art. Illustratively, screening for activity of an enzyme illustratively includes contacting an enzyme with a natural or synthetic substrate of an enzyme and measuring the enzymatic cleavage of the substrate. Illustrative substrates for this purpose include casein, which is cleaved by a protease to liberate folin-positive amino acids and peptides (calculated as tyrosine) that are readily measured by techniques known in the art. The synthetic substrate furylacryloylated tripeptide 3-(2-furylacryloyl)-L-glycyl-L-leucine-L-alanine obtained from Bachem AG, Bubendorf, Switzerland is similarly operable. Illustrative substrates of α-amylase include long chain carbohydrates such as amylose or amylopectin that make up starch. Other methods of screening for α-amylase activity include the colorimetric assay of Fischer and Stein, *Biochem. Prep.,* 1961, 8, 27-33. It is appreciated that one of ordinary skill in the art can readily envision methods of screening for enzyme activity with the enzyme present in or on a variety of materials.

A protein is illustratively recombinant. Methods of cloning, synthesizing or otherwise obtaining nucleic acid sequences encoding a protein are known and standard in the art. Similarly, methods of cell transfection and protein expression are similarly known in the art and are applicable herein. Exemplary cDNA encoding the protein sequence of SEQ ID NO: 1 is the nucleotide sequence SEQ ID NO: 2. Exemplary cDNA encoding the protein sequence of SEQ ID NO: 3 is the nucleotide sequence found at accession number M11446 and SEQ ID NO: 4. Exemplary cDNA encoding the protein sequence of SEQ ID NO: 5 is the nucleotide sequence SEQ ID NO: 6

A protein may be coexpressed with associated tags, modifications, other proteins such as in a fusion protein, or other modifications or combinations recognized in the art. Illustrative tags include 6×His, FLAG, biotin, ubiquitin, SUMO, or other tag known in the art. A tag is illustratively cleavable such as by linking to protein via a target sequence that is cleavable by an enzyme known in the art illustratively including Factor Xa, thrombin, SUMOstar protein as obtainable from Lifesensors, Inc., Malvern, Pa., or trypsin. It is further appreciated that chemical cleavage is similarly operable with an appropriate cleavable linker.

Protein expression is illustratively accomplished following transcription of a protein nucleic acid sequence, translation of RNA transcribed from the protein nucleic acid sequence or analogues thereof. An analog of a nucleic acid sequence is any sequence that when translated to protein will produce a wild-type protein or an analogue of a wild-type protein. Protein expression is optionally performed in a cell based system such as in *E. coli*, Hela cells, or Chinese hamster ovary cells. It is appreciated that cell-free expression systems are similarly operable.

It is recognized that numerous analogues of protein are operable including amino acid substitutions, alterations, modifications, or other amino acid changes that increase, decrease, or not do alter the function of the protein sequence. Several post-translational modifications are similarly envisioned as within the scope of the present specification illustratively including incorporation of a non-naturally occurring amino acid, phosphorylation, glycosylation, addition of pendent groups such as biotin, avidin, fluorophores, lumiphores, radioactive groups, antigens, or other molecules.

A protein according to the specification is chemically modified by the addition of one or more polymeric moieties. Polymeric moieties optionally have a molecular weight ranging from 200 to 100,000 Daltons. Polymeric moieties optionally have a molecular weight ranging from 10,000 to 100,000 Daltons. Polymeric moieties are optionally linear, branched, liable, or combinations thereof. The polymeric moieties are optionally homomeric or heteromeric. Illustrative examples of polymeric moieties include one or more molecules of carbohydrate or polyoxyethylene (otherwise known as polyethylene glycol or "PEG").

Illustrative examples of polymeric moieties include but are not limited to: polyalkyl alcohols and glycols (including heteroalkyl with, for example, oxygen) such as polyoxyethylenes and polyoxyethylene derivatives, dextrans including functionalized dextrans; styrene polymers; polyethylene and derivatives; polyanions including, but not limited to, polymers of heparin, polygalacturonic acid, mucin, nucleic acids and their analogs including those with modified ribosephosphate backbones, polypeptides of glutamate, aspartate, or combinations thereof, as well as carboxylic acid, phosphoric acid, and sulfonic acid derivatives of synthetic polymers; and polycations, including but not limited to, synthetic polycations based on acrylamide and 2-acrylamido-2 methylpropanetrimethylamine, poly(N-ethyl-4-vinylpyridine) or similar quarternized polypyridine, diethylaminoethyl polymers and dextran conjugates, polymyxin B sulfate, lipopolyamines, poly(allylamines) such as the strong polycation poly(dimethyldiallylammonium chloride), polyethyleneimine, polybrene, spermine, spermidine and proteins such as protamine, the histone polypeptides, polylysine, polyarginine and polyornithine; and mixtures and derivatives thereof. Suitable additional polymers are outlined in Roberts, M. J. et al. (2002) "Chemistry for peptide and protein PEGylation" Adv. Drug Deliv. Rev. 54, 459-476; Kinstler, O. et al. (2002) "Mono-N-terminal poly(ethylene glycol)-protein conjugates" Adv. Drug Deliv. Rev. 54; U.S. Application Ser. No. 60/360,722; U.S. Pat. Nos. 5,795,569; 5,766, 581; EP 01064951; U.S. Pat. No. 6,340,742; WO 00176640; WO 002017; EP0822199A2; WO 0249673A2; U.S. Pat. Nos. 4,002,531; 5,183,550; 5,985,263; 5,990,237; 6,461, 802; 6,495,659; 6,448,369; 6,437,025; 5,900,461; 6,413, 507; 5,446,090; 5,672,662; 6,214,966; 6,258,351; 5,932, 462; 5,919,455; 6,113,906; 5,985,236; WO 9428024A1; U.S. Pat. Nos. 6,340,742; 6,420,339; and WO 0187925A2.

Polyoxyethylene includes the generic structure —$(CH_2CH_2O)_n$—, where n is an integer optionally from 2 to 2000. Optionally, n is an integer ranging from 50 to 500, optionally from 100 to 250, optionally from 150 to 250. Polyoxyethylene is optionally provided in a range of sizes attached to proteins using one or more of a variety of chemistries known in the art. Polyoxyelthylenes are optionally covalently associated with primary amines (e.g. lysine side chains or the protein N-terminus), thiols (cysteine residues), or histidines. Lysine occurs frequently on the surface of proteins, so binding of polyoxyethylene at lysine side chains produces a mix of reaction products. Since the pKa of the N-terminus is significantly different than the pKa of a typical lysine side chain, it is possible to specifically target the N-terminus for modification. Similarly, as most proteins contain very few free cysteine residues, cysteines (naturally occurring or engineered) may be targeted for site-specific interactions with polyoxyethylene.

Polyoxyethylene is optionally end capped where one end is end-capped with a relatively inactive group such as an alkoxy group, while the other end is a hydroxyl group that may be further modified by linker moieties. When the term "PEG" is used to describe polyoxyethylene the term "PEG" may be followed by a number (not being a subscript) that indicates a PEG moiety with the approximate molecular weight equal the number. Hence, "PEG10000" is a PEG moiety having an approximate molecular weight of 10,000 Daltons. The inventors have found that some aspects including linear PEG10000 are superior to other PEG molecules. In some bases, enzymes that are covalently associated with a branched PEG, optionally an 8-arm branched PEG, produces superior resistance to weathering by contact or immersion in water.

The term "PEGylation" as used herein denotes modification of a protein by attachment of one or more PEG moieties via a linker at one or more amino acids. The polyoxyethylene (PEG) moiety is illustratively attached by nucleophilic substitution (acylation) on N-terminal α-amino groups or on lysine residue(s) on the gamma-positions, e.g., with PEG-succinimidyl esters. Optionally, polyoxyethylene moieties are attached by reductive alkylation—also on amino groups present in the protein using PEG-aldehyde reagents and a reducing agent, such as sodium cyanoborohydride. Optionally, polyoxyethylene moieties are attached to the side chain of an unpaired cysteine residue in a Michael addition reaction using for example PEG maleimide reagents. Polyoxyethylene moieties bound to a linker are optionally available from JenKem Technology USA, Allen, Tex. It is appreciated that any PEG molecule taught in U.S. Application Publication No: 2009/0306337 is operable herein. U.S. Application Publication No: 2009/0306337 also teaches methods of attaching PEG groups to a protein. PEG is optionally linked to a protein via an intermediate ester, amide, urethane, or other linkage dependent on the choice of PEG substrate and position of modification on a protein.

In some aspects, a protein is an analogue of a hydrolase with the inclusion of additional cysteines to provide site specific incorporation sites for polyoxyethylene. In some aspects, lysine or histidine residues are substituted with alternative amino acids that do not possess a target primary amine so as to prevent binding of a molecule of polyoxyethylene at that site. The choice of amino acid residues such as cysteines, lysines, or histidines to remove depends on the desired extent of modification. Optionally, simulation computer programs are used to predict whether modification with a polymer will interfere with the function of the protein as described in U.S. Pat. No. 7,642,340.

Proteins as used herein are optionally mono-substituted i.e. having only one polymeric moiety attached to a single amino acid residue in the protein molecule or to a N-terminal amino acid residue. Alternatively, two, three, four, or more polymeric moieties are present on a single protein. In aspects where protein includes more than one polymeric moiety, it optionally has the same moiety attached to each associated amino acid group or to the N-terminal amino acid residue. However, the individual polymer groups may also vary from each other in size and length and differ between locations on the protein.

Reversible binding of one or more polymeric moieties at one or more sites on a protein is optionally used. In these aspects, the polymer is covalently attached but is liable upon exposure to weathering such as for example heating, water washing, or simply over time. The liable bond is optionally the bond between the protein and the polymer or within a linker present between a protein and a polymer.

An inventive process optionally include one or more active chemically modified proteins incorporated into a base to form a coating material. The protein is optionally non-covalently associated and/or covalently attached to the base material or is otherwise associated therewith such as by bonding to the surface or by intermixing with the base material during manufacture such as to produce entrapped protein. In some aspects, the protein is covalently attached to the base material either by direct covalent interaction between the protein and one or more components of the base material or by association via a linker.

There are several ways to associate protein with a base in a coating. One of which involves the application of covalent bonds. Specifically, free amine groups of the protein are optionally covalently bound to an active group of the base. Such active groups include alcohol, thiol, aldehyde, carboxylic acid, anhydride, epoxy, ester, or any combination thereof. This method of incorporating protein delivers unique advantages. First, the covalent bonds tether the proteins permanently to the base and thus place them as an integral part of the final composition with much less, if any at all, leakage of the protein. Second, the covalent bonds provide extended enzyme lifetime. Over time, proteins typically lose activity because of the unfolding of their polypeptide chains. Chemical bonding such as covalent bonding effectively restricts such unfolding, and thus improves the protein life. The life of a protein is typically determined by comparing the amount of activity reduction of a protein that is free or being physically adsorbed with that of a protein covalently-immobilized over a period of time.

A protein is optionally associated with a base at a ratio of 1:1 to 1:20 (enzyme:base) by weight. Optionally, a protein is associated with a base at a ratio of 1:2 to 1:15, optionally 1:4 to 1:12 by weight.

Proteins are optionally uniformly dispersed throughout the substrate network to create a homogenous protein platform.

Chemical methods of protein attachment to materials will naturally vary depending on the functional groups present in the protein and in the material components. Many such methods exist. For example, methods of attaching proteins (such as enzymes) to other substances are described in O'Sullivan et al, *Methods in Enzymology*, 1981; 73:147-166 and Erlanger, *Methods in Enzymology*, 1980; 70:85-104.

Proteins are optionally present in a coating that is layered upon a substrate wherein the protein is optionally entrapped in the base material, admixed therewith, modified and integrated into the base material or layered upon a base material.

A water-stabilized coating composition optionally includes one or more additives, optionally for modifying the properties of the composition material. Illustrative examples of such additives include one or more light stabilizers such as a UV absorber or radical scavenger illustratively including those described in U.S. patent application Ser. No. 13/024,794 or U.S. Pat. No. 5,559,163, a plasticizer, a wetting agent, a preservative, a surfactant, a lubricant, a pigment, a filler, and an additive to increase sag resistance.

An inventive process optionally includes overlayering (coating) a substrate with a water-stabilized active coating material such that the protein is capable of enzymatically degrading a component of an organic stain in contact with the active coating material. A substrate is any surface capable of being coated with an inventive coating. A substrate is optionally flexible or rigid with flexibility relative to that of a polyvinylchloride sheet with a thickness of 10 mm. A substrate has a first surface and a second surface wherein the first surface and the second surface are opposed. A coating is optionally overlayered on a substrate on a first surface, a second surface, both, or fully encapsulates a substrate. The coating of a substrate with a water-stabilized active coating material provides a self-cleaning surface that promotes the removal or loosening of an organic stain when present on the coating.

The identity of a substrate is limited only by its ability to be coated with an inventive composition. Illustratively, a substrate is metal, wood, natural or synthetic polymers such as fiberglass or other plastics, resins, paints, lacquers, stone, leather, other material, or combinations thereof. A substrate is optionally an automotive body panel or portion thereof. A substrate is optionally a boat hull or portion thereof. A substrate is optionally a wood floor or a coated wood floor. A substrate optionally includes a subcoating such as wood coated with a polyurethane protectant, or a subcoating is a paint, varnish, or other protectant commonly found on substrate. A water-stabilized active coating material optionally contacts the substrate by overlaying the subcoating material.

Water-stabilized coatings as provided herein provide good adhesion to substrates, protection against environmental insults, protection against corrosion, and further provide active properties of the protein. Thus, in certain aspects, coatings of water-stabilized active coating material provide enzyme activity on a substrate useful in numerous applications such as detection of an analyte which is a substrate for the enzyme or a ligand for a receptor, antibody or lectin. In some aspects, coatings provide resistance against staining by enzyme digestion of one or more components of stain producing material.

When a water-stabilized composition is contacted with biological, food, or environmental material to produce an organic stain, the enzyme or combinations of enzymes contact the stain, or components thereof. The contacting allows the enzymatic activity of the protein to interact with and enzymatically alter components of the stain improving its removal from the substrate or coating.

Proteins are included in compositions as provided herein in amounts ranging from 0.1-50, 1-30, 1-20, 1-10, 2-8, 3-6, or other weight percent of the total weight of the material composition.

Enzyme containing coatings have a surface activity generally expressed in Units/cm$^2$. Coatings including a thermolysin such as THERMOASE C160 (thermolysin from *Bacillus stearothermophilus*) optionally have functional surface activities prior to exposure to water of greater than 0.0075 Units/cm$^2$. In some aspects, thermolysin surface activity is between 0.0075 Units/cm$^2$ and 0.05 Units/cm$^2$ or any value or range therebetween. Optionally, thermolysin surface activity is between 0.0075 Units/cm$^2$ and 0.1 Units/cm$^2$ or any value or range therebetween. Optionally, thermolysin surface activity is between 0.01 Units/cm$^2$ and 0.05 Units/cm$^2$ or any value or range therebetween. In coatings containing α-amylase from *Bacillis subtilis*, typical surface activities prior to exposure to water are at or in excess of 0.01 Units/cm$^2$. In some aspects, α-amylase surface activity is between 0.01 Units/cm$^2$ and 1.5 Units/cm$^2$ or any value or range therebetween. Optionally, α-amylase surface activity is between 0.01 Units/cm$^2$ and 2.5 Units/cm$^2$ or any value or range therebetween. Optionally, α-amylase surface activity is between 0.01 Units/cm$^2$ and 1.0 Units/cm$^2$ or any value or range therebetween. In some aspects, α-amylase surface activity is at or between 0.01 Units/cm$^2$ and 4.0 Units/cm$^2$. It is appreciated that higher surface activities are achievable by increasing the enzyme concentration, using enzyme with a higher specific activity such as an analogue of a wild-type enzyme, or by otherwise stabilizing enzyme activity during association with a base material.

It is appreciated that the inventive processes of facilitating stain removal will function at any temperature whereby the protein is active. Optionally, the inventive process is performed at 4° C. Optionally, an inventive process is performed at 25° C. Optionally, an inventive process is performed at ambient temperature. It is appreciated that the inventive process is optionally performed from 4° C. to 125° C., or any single temperature or range therebetween.

The presence of protein combined with the material of a substrate or a coating on a substrate, optionally, with water or other fluidic rinsing agent, breaks down stains for facilitated removal.

An inventive process includes providing a coating with an enzyme such that the enzyme is enzymatically active and capable to cleave or otherwise modify one or more components of an organic stain. In particular aspects, an organic stain is based on organic matter such as that derived from an insect optionally an insect body, a fingerprint, foodstuffs, or from the environment.

An organic stain as defined herein is a stain, mark, or residue left behind after an organism, food, or environmental agent contacts a coating. An organic stain is not limited to marks or residue left behind after a coating is contacted by an insect body. Other sources of organic stains are illustratively: insect wings, legs, or other appendages; bird droppings; food or components of food; fingerprints or residue left behind after a coating is contacted by an organism; or other sources of organic stains such as bacteria or molecules present in water (or aqueous solvent) or soil.

Methods of preparing water-stabilized active coating materials illustratively include association of aqueous solutions of protein and commercially available base materials by mixing such as by propeller mixing or hand mixing to a uniform or a non-uniform distribution of chemically modified protein to produce water-stabilized coating materials.

Various aspects are illustrated by the following non-limiting examples. The examples are for illustrative purposes and are not a limitation on any practice. It will be understood that variations and modifications can be made without departing from the spirit and scope of the specification.

Example 1

Materials for Production of Water-Stabilized Active Coating Material.

Materials: α-Amylase KLEISTASE SD80 from *Bacillus subtilis* (EC 3.2.1.1), lipase (lipase A12 (E.C.3.1.1.3) from *Aspergillus niger*), Protease N, Protease A, Protin SD AY-10, *B. sterothermophilus* TLP (THERMOASE C160), and THERMOASE GL30 (low activity preparation of *B. sterothermophilus* TLP) are obtained from AMANO Enzyme Inc. (Nagoya, JAPAN). Bovine serum albumin (BSA) from bovine serum, starch from potatoes, starch from wheat, maltose, sodium potassium tartrate, 3,5-dinitrosalicylic acid, $Na_2(PO_4)$, NaCl, $K_2(PO_4)$, casein, trichloroacetic acid, Folin & Ciocalteu's phenol reagent, $Na_2(CO_3)$, sodium acetate, calcium acetate, tyrosine, p-nitrophenyl palmitate, ethanol, iodine, glucose, maltose, maltotriose, maltohexose, dextrin (10 kDa and 40 kDa) are obtained from Sigma Chemical Co., St. Louis, Mo., U.S.A. Aluminum panels and 8-path wet film applicator are purchased from Paul N. Gardner Company, Inc. (Pompano Beach, Fla.). An Oster blender (600 watts) and light mayonnaise are obtained from a local supermarket. Freeze-dried crickets are obtained from Fluker Laboratories (Port Allen, La.). Polyethylene glycol (PEG) derivatives with succinimidyl ester of different molecular weights are obtained from Fishersci (Pittsburgh, Pa.).

Polyacrylate resin Desmophen A870 BA, and the crosslinker hexamethylene diisocyanate (HDI) based polyfunctional aliphatic polyisocyanate resin Desmodur N 3600 are obtained from Bayer Corp. (Pittsburgh, Pa.). The surfactant BYK-333 is obtained from BYK-Chemie (Wallingford, Conn.). 1-butanol and 1-butyl acetate are obtained from Sigma-Aldrich Co. (Missouri, USA). Aluminum paint testing panels are purchased from Q-Lab Co. (Cleveland, USA). All other reagents involved in the experiments are of analytical grade.

Example 2

Preparation of Enzymes.

Lipase, α-amylase, and thermolysin are each prepared by ultrafiltration from raw powder. For α-amylase, a 150 mL solution from raw powder (6.75 g) is prepared in DI water. For thermolysin, a 150 mL solution of 1.5 g $B.$ $sterothermophilus$ thermolysin-like-protease (TLP) is prepared in DI water. For lipase, a 150 mL solution of 1.5 g lipase A12 is prepared in DI water. The insoluble large impurity in raw powder is removed by filtration over a 200 nm PTFE filter. The obtained solution has a protein concentration of 20 mg/mL (measured by the Bradford method) and is maintained on ice.

Ultrafiltration is performed using a 150 mL Amicon cell (cooled with ice) with a pressure of 55 psi and an ultrafiltration membrane with a cut-off of 30 kDa from Millipore (Billerica, Mass.). Ultrafiltration is repeated 3 times by refilling the cell back to 150 mL of 50 mM Phosphate Buffered Saline (PBS), pH=7.5 after each run. The final remaining purified protein solution is quantified by the Bradford method and diluted to the final working concentration used for chemical modification and production of coating materials in 50 mM PBS, pH=7.5. Coatings are made using a solution of 50, 100, 200, or 300 mg/mL of purified enzyme prior to or following chemical modification with one or more polymeric moieties.

Example 3

PEGylation of enzyme. Purified enzyme (1 mL, 140 mg/ml) (α-amylase, thermolysin, or lipase) is mixed with PEG (monofunctional linear PEG10000, PEG12000, PEG20000, or 8-arm branched PEG (PEG N-Hydroxysuccinimide ester purchased from NANOCS Inc. (New York, N.Y.), in DMSO) derivatized with succinimidyl ester at a mole ratio of 1:5 enzyme:PEG. The 8-arm branched PEG has a molecular weight of 10,000 Daltons with a comb-shape structure. Each branch has a molecular weight of ~1,200 Daltons. The structure of the 8-arm branched PEG has the following structure:

The reaction mixture is incubated in an ice bath for 4 hours under magnetic stirring at 800 rpm. Byproducts are removed by ultrafiltration (50K cutoff MW). Enzyme concentration is adjusted to 140 mg/ml for preparation of coating materials, to 1 mg/ml for SDS-PAGE, and to 0.1 mg/ml for activity assays. Some preparations further involve isolation of non-reacted PEG by filtration with a filter with an appropriate molecular weight cut-off for each PEG used in the PEGylation reactions.

Example 4: Preparation of Coating Materials

Either unmodified (optionally fluorescently labeled) or PEG modified (optionally fluorescently labeled) α-amylase, thermolysin, lipase or combinations of enzymes are prepared in solution solution (600 μL, 140 mg/ml) as in Example 3 and admixed to 2.1 g Desmodur A870 together with 500 μL n-butyl acetate and 100 μL surfactant (17% v/v in butyl acetate) under vigorous stirring for 1 min by IKA RW 11 Lab-egg stirrer. The resulting whitish emulsion is subsequently added to 0.8 g Desmophen N3600 and again vigorously mixed for 1 min.

Test panels are coated with a coating composition by drawn-down application of wet film using an 8-path wet film applicator from Paul N. Gardner (Pompano Beach, Fla.) in the predetermined thickness of 20 μm onto aluminum panels or aluminum foil. The resultant coating is flashed 10 minutes in air and then cured in oven at 70° C. for 4 hours. An illustrative process of preparing a water-stabilized bioactive coating composition and applying the composition to a substrate is illustrated in FIG. 1.

Figure 2A:
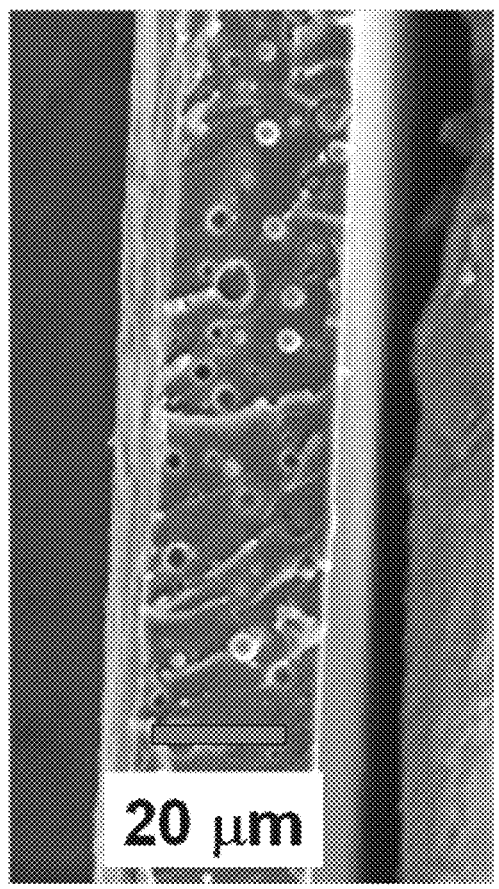
FIG. 2A illustrates large particles formed in a 2K SB coating material when the enzyme is incorporated into the coating material in the absence of a polymeric moiety as depicted by scanning electron microscopy.
Figure 2B:
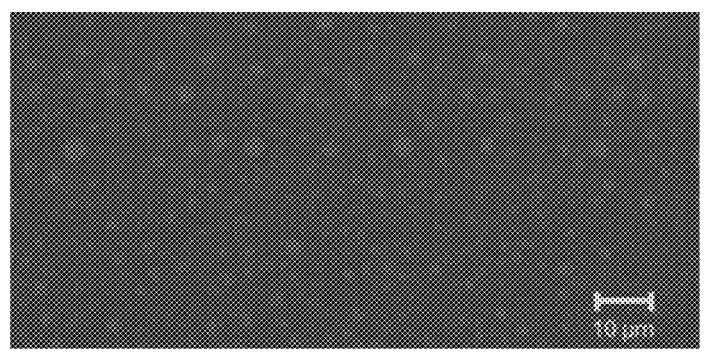
FIG. 2B illustrates large particles formed in a 2K SB coating material when the enzyme is incorporated into the coating material in the absence of a polymeric moiety as depicted by scanning fluorescence microscopy.
Figure 3A:
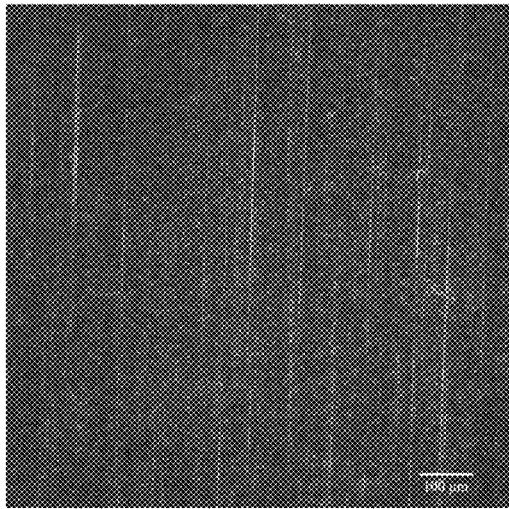
FIG. 3A illustrates effective dispersion of a chemically modified enzyme into a base according to one aspect using enzyme modified by polyoxyethylene.
Figure 3B:
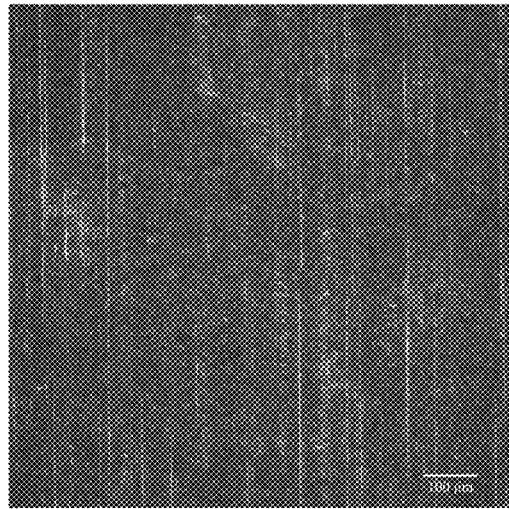
FIG. 3B illustrates effective dispersion of a chemically modified enzyme into a base according to one aspect using enzyme modified by polyoxyethylene.
Figure 3C:
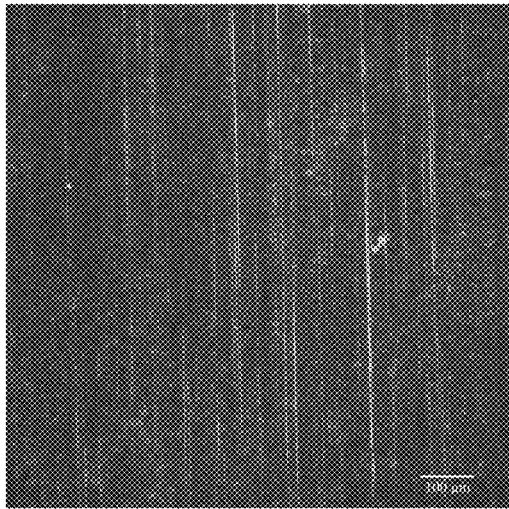
FIG. 3C illustrates effective dispersion of a chemically modified enzyme into a base according to one aspect using enzyme modified by polyoxyethylene.
Figure 3D:
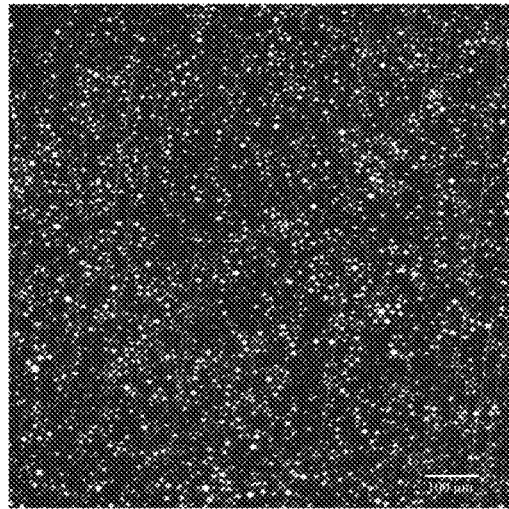
FIG. 3D illustrates effective dispersion of an unchemically modified enzyme into a base.

Coatings on the substrates are analyses by both fluorescent microscopy and scanning electron microscopy (SEM) to determine the enzyme dispersion in the base materials. For SEM characterization, cross-sectionized samples are prepared by coating on the heavy duty Reynolds Wrap® aluminium foil (Richmond, Va.) using an applicator. The fully cured coatings are torn and the resulting cross-sections of the fractured polymers are sputtered with Au—Pd. The unchemically modified (e.g. not PEGylated) enzymes show large average particle formation in excess of 5 μm. FIGS. 2A and B. In contrast, the enzymes that are modified by polyoxyethylene show much reduced average particle sizes indicating dispersion of the enzyme in the base materials. FIG. 3A-C (D is a non-chemically modified example).

In other aspects, enzyme is intermixed with polyoxyethylene at similar concentrations to the covalently associated molecules, but without covalent attachment of the enzyme to the polymeric moiety. The enzyme/polymeric moiety solution is intermixed with base and cured as above. FIG. 4 illustrates dispersion of the enzyme in the base material both when covalently associated with the PEG and when non-

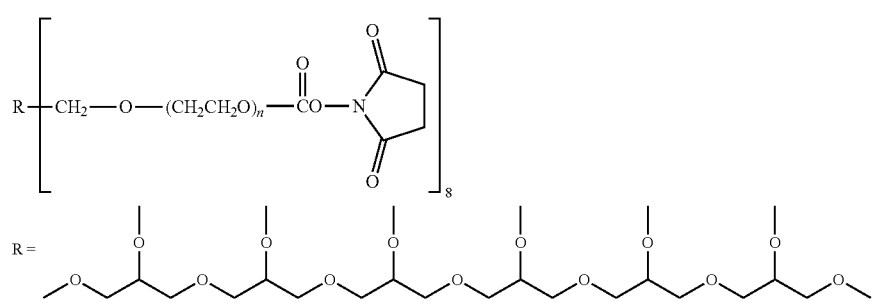

Figure 4A:
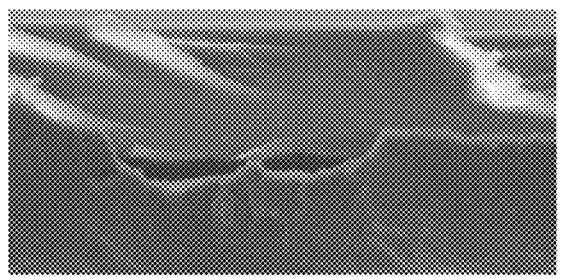
FIG. 4A illustrates a coating formed in the absence of enzyme or a polymeric moiety.
Figure 4B:
FIG. 4B illustrates the presence of PEG intermixed with enzyme dispersed in the coating.
Figure 4C:
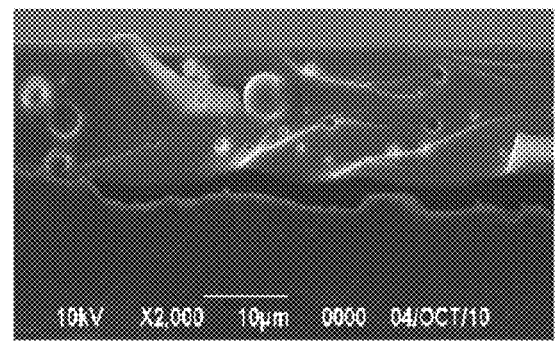
FIG. 4C illustrates the large particles formed when enzyme (unmodified) is incorporated into a coating.
Figure 4D:
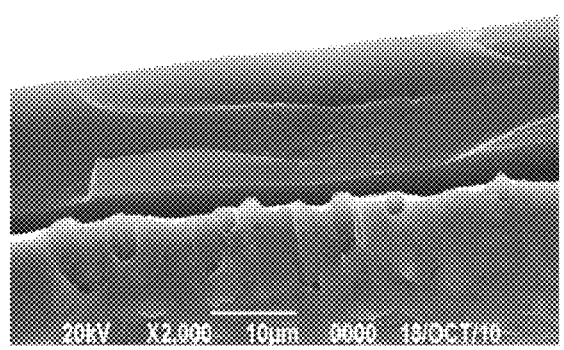
FIG. 4D illustrates the excellent dispersion of PEGylated enzyme in base material (D) demonstrating superior dispersion of enzyme relative to the absence of a polymeric moiety associated with the enzyme.

(I)

covalently associated with the PEG. FIG. 4A illustrates base material intermixed with PEG alone. FIG. 4B illustrates physical intermixing, but non-covalently associated enzyme with PEG demonstrating excellent dispersion of the enzyme in the base material. FIG. 4C illustrates unchemically modified enzyme in base material in the absence of a polymeric moiety illustrating the lack of dispersion of enzyme in the base material. FIG. 4D illustrates covalently associated PEG dispersed in base material demonstrating superior dispersion of enzyme relative to the absence of a polymeric moiety associated with the enzyme.

Example 5: Water Weathering Durability of Coatings

Coated aluminum panels formed as in Example 4 are cut to test size of 1.2 cm×1.9 cm and subjected to weathering by submersion in room temperature DI water for 30 minutes with agitation. The test panels are removed and rinsed with flowing DI water for 20 seconds followed by assay for remaining enzyme activity. The immersion is repeated between 2 and 10 times and the remaining enzyme activity assayed.

Test panels coated with α-amylase containing coatings are assayed by determination of amydolytic activity by reacting test panels with the α-amylase substrate 1% w/v potato starch in 20 mM sodium phosphate buffer with 6.7 mM sodium chloride (pH 6.9). The substrate solution (2 mL) is added to one rectangular piece of the coated test panel (1.2 cm×1.9 cm) and incubated for 3 min at 25° C. The equivalent amount of reducing sugar produced is determined using a UV-VIS spectrometer (Cary 300-Varian Inc., Walnut Creek, Calif., USA) at 540 nm. One unit of α-amylase activity is defined as 1.0 mg of reducing sugar (calculated from a standard curve previously calibrated against maltose) released from starch in 3 min at room temperature.

Coatings prepared with thermolysin are assayed for proteolytic surface activity essentially following the method of Folin and Ciocalteau, *J. Biol. Chem.*, 1927; 73: 627-50. Briefly, 1 mL of 2% (w/v) casein in sodium phosphate (0.05 M; pH 7.5) buffer solution is used as substrate together with 200 µl of sodium acetate, 5 mM calcium acetate (10 mM; pH 7.5). The substrate solution is pre-incubated in a water bath for 3 min to reach 37° C. The reaction is started by adding one piece of sample plate coated with *B. sterothermophilus* TLP based coating (1.2×1.9 cm) followed by shaking for 10 min at 200 rpm at which time the reaction is stopped by adding 1 ml of 110 mM trichloroacetic acid (TCA) solution. The mixture is incubated for 30 min at 37° C. prior to centrifugation. The equivalent of tyrosine in 400 µL of the TCA-soluble fraction is determined at 660 nm using 200 µL of 25% (v/v) Folin-Ciocalteau reagent and 1 mL 0.5 M sodium carbonate. One unit of activity is defined as the amount of enzyme hydrolyzing casein to produce absorbance equivalent to 1.0 µmol of tyrosine per minute at 37° C. This result is converted to Units/cm$^2$.

Figure 5:
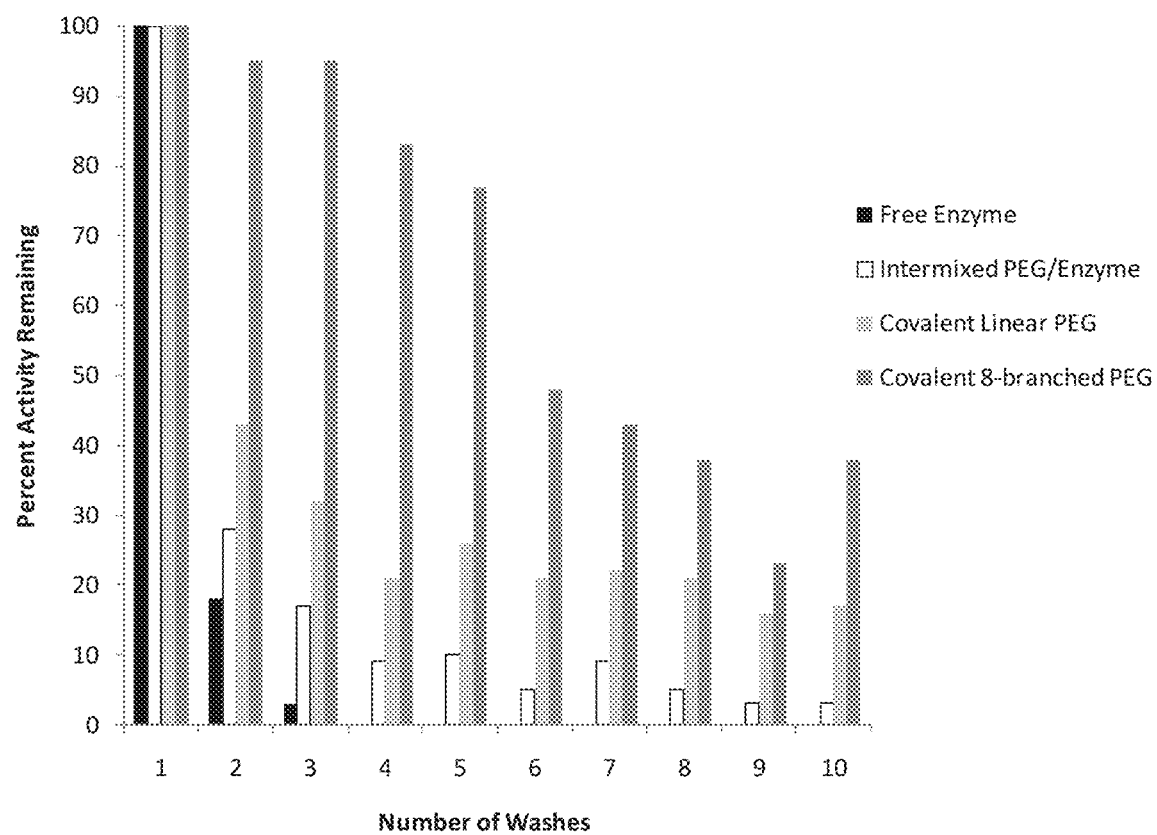
FIG. 5 illustrates water-stability of a coating incorporating a chemically modified enzyme as measured by residual coating surface activity after water the indicated number of water immersions.

An exemplary residual activity depicting the water-stability of coating preparations bases on α-amylase is depicted in FIG. 5. The coatings containing unmodified α-amylase lose more than 80 percent of the base activity after a second wash (black bars). Following a fourth wash, the remaining activity is undetectable. In coating formulations where the enzyme is intermixed (non-covalently attached) with PEG and the intermixed solution is then dispersed into the base (white bars), significant levels of activity remain in the coating relative to coatings formed in the absence of PEG. Activity remains detectable after 10 washes. Covalent attachment of linear PEG molecules onto the α-amylase produces a coating that is highly resistant to activity loss with greater than 30% enzyme activity remaining after three washes (light gray bars) compared to the unmodified enzyme based coatings that are nearly inactive after three washes. The greatest relative activity levels are maintained when α-amylase is covalently associated with a branched PEG molecule. FIG. 5 illustrates approximately 40% enzyme activity remaining after 10 washes (dark gray bars). These data demonstrate that the presence of a polymeric moiety with the enzyme in a coating composition leads to resistance to inactivation by immersion in water.

Example 6

Preparation of organic stains and application to coated substrate and self-cleaning activity of coating preparations. For preparation of insect matter, 60 g of Freeze-dried crickets are chopped into powder by a blender (Oster, 600 watt) for 10 min. The stain solution is prepared by vigorously mixing 2 grams of cricket powder with 6 mL of DI water. A template of uniform spacing is used to apply the stain on the coating surface. The cricket stains are dried at 40° C. for 5 min. Each test panel is placed into a glass dish subjected to rinsing with 200 mL of DI water under 300 rpm shaking at RT for various times. The time of the stain removal is recorded. In order to reduce random error, the time of the first and last drop removed are not included. The average rinsing time of eight stain spots is averaged for stain removal time. Test panels coated with PEGylated thermolysin containing coatings provide improved stain removal by gentle rinsing as compared to panels coated with base material alone.

Amylase containing coatings of are placed on the plastic surfaces of standard compact disks or aluminum test panels as in Example 4. A 0.3 g sample of light mayonnaise is placed on various sections of the test panels followed by air dry at ambient conditions for 2 minutes prior to standing upright. Light mayonnaise includes large macromolecules such as fat and starch that contribute to its high viscosity and thus to the high frictional force on the coating surface that prevents gravity driven sliding of the mayonnaise when the test panel is tilted vertically. Coatings containing modified α-amylase catalyze the hydrolysis of the emulsifier resulting in tremendously lowered viscosity as a consequence of a phase separation at the stain-coating interface, thus allowing the stain to slide down the test panel when tilted vertically.

Similarly, aluminum test panels are coated with PEGylated α-amylase, PEG with no enzyme, or a coating with no enzyme or PEG as a control. Some test panels are immersed in water between 1 and 5 times as in Example 5 prior to contacting with a stain material. A drop of light mayonnaise is then placed on the panel, the panel is placed in a vertical position and any gravity driven movement of the light mayonnaise spot are monitored. The test panels coated with enzyme free coating or PEG only coatings show no movement of the light mayonnaise following tilting to a vertical position indicating the absence of coating bioactivity. The coating with PEGylated enzyme, however, shows significant self-cleaning as illustrated by lower adherence of the mayonnaise resulting in the spot moving down the test panel. The self-cleaning aspects of the coatings are also maintained after each of the water immersions.

The coatings of Example 4 containing PEGylated lipase are used to test removal of fingerprints from glass or transparent plastic surfaces. The self-cleaning of fingerprints by PEGylated lipase containing preparations is tested on glass substrates. Test panels are coated with either PEGylated lipase containing base materials or control materials (no enzyme) and incubated at room temperature 24 hours. In some experiments the coated surfaces are immersed in water between 1 and 5 times as in Example 5. The test panels are stained with human fingerprints or facial skin contact. The coated test panels are then incubated in an oven at 120° C. for 1 to 6 hours. For better visualization of any remaining fingerprints, coatings are washed under running DI water (50 mL/sec) for 1 minute and dried using air. Prior to heating each coating is subjected to the same level of staining by fingerprints. Following baking, coatings without enzyme show significant residual staining while coatings containing PEGylated lipase show greatly reduced stain remaining with the level of residual fingerprint staining reduced with increased enzyme concentration. The level of stain removal is also maintained for test panels that were immersed in water.

Various modifications of the present specification, in addition to those shown and described herein, will be apparent to those skilled in the art of the above description. Such modifications are also intended to fall within the scope of the appended claims.

It is appreciated that all reagents are obtainable by sources known in the art unless otherwise specified or synthesized by one of ordinary skill in the art without undue experimentation. Methods of protein production and purification are similarly within the level of skill in the art.

REFERENCE LIST

Harris, J. M. and Kozlowski, A. (2001). Improvements in protein PEGylation: pegylated interferons for treatment of hepatitis C. *J. Control Release* 72, 217-224.

Veronese, F. and Harris, J. M. Eds. (2002). Peptide and protein PEGylation. Advanced Drug Delivery Review 54(4), 453-609.

Veronese, F. M.; Pasut, G. (2005), PEGylation, successful approach to drug delivery, *Drug Discovery Today* 10 (21): 1451-1458.

Veronese, F. M.; Harris, J. M. (2002), Introduction and overview of peptide and protein pegylation, *Advanced Drug Delivery Reviews* 54 (4): 453-456.

Damodaran V. B.; Fee C. J. (2010), Protein PEGylation: An overview of chemistry and process considerations, *European Pharmaceutical Review* 15 (1): 18-26.

Harris, J. M.; Chess, R. B. (2003), Effect of pegylation on pharmaceuticals. *Nature Reviews Drug Discovery* 2, 214-221.

Rodriguez-Martinez J. A., et. al. (2008) Stabilization of a-Chymotrypsin Upon PEGylation. Correlates With Reduced Structural Dynamics. *Biotechnology and Bioengineering*, 101, 1142-1149.

Li, J.; Kao, W. J. (2003), Synthesis of Polyethylene Glycol (PEG) Derivatives and PEGylated-Peptide Biopolymer Conjugates. *Biomacromolecules* 4, 1055-1067.

United States Patent Application Publication Number 2010/0279376.

United States Patent Application Publication Number 2008/0293117.

Patents and publications mentioned in the specification are indicative of the levels of those skilled in the art to which the specification pertains. These patents and publications are incorporated herein by reference to the same extent as if each individual patent or publication was specifically and individually incorporated herein by reference.

The foregoing description is illustrative of particular aspects of compositions or methods, but is not meant to be a limitation upon the practice thereof. The following claims, including all equivalents thereof, are intended to define the scope of the invention.

The invention claimed is:

1. A water-stabilized bioactive coating composition comprising:
   a base;
   a first polyoxyethylene associated with said base; and
   an enzyme associated with said base;
   wherein said enzyme is associated with one or more molecules of a second polyoxyethylene to form a chemically modified enzyme, the second polyoxyethylene having a molecular weight from 10,000 Daltons to 100,000 Daltons;
   wherein said base, said enzyme, and said first polyoxyethylene form a water-stabilized active coating composition.

2. The composition of claim 1 wherein said enzyme is a hydrolase.

3. The composition of claim 2 wherein said hydrolase is a bacterial neutral thermolysin-like-protease, an amylase, a lipase, or combinations thereof.

4. The composition of claim 1 wherein said first polyoxyethylene has a molecular weight between 1,000 and 15,000 Daltons.

5. The composition of claim 1 wherein said first polyoxyethylene and said second polyoxyethylene have equal polymers of oxyethylene.

6. The composition of claim 1 wherein said second polyoxyethylene is covalently attached to said enzyme via an intermediate urethane linkage.

7. The composition of claim 1 wherein said second polyoxyethylene has a molecular weight of 10,000 Daltons to 20,000 Daltons.

8. The composition of claim 1 wherein said second polyoxyethylene has a molecular weight of 12,000 Daltons to 100,000 Daltons.

9. The composition of claim 1 wherein said second polyoxyethylene is an eight-arm polyoxyethylene.

* * * * *